(12) United States Patent
Geneste et al.

(10) Patent No.: US 8,268,815 B2
(45) Date of Patent: Sep. 18, 2012

(54) PYRIMIDINE COMPOUNDS AND USE THEREOF

(75) Inventors: Hervè Geneste, Neuhofen (DE); Andreas Haupt, Schwetzingen (DE); Wilfried Braje, Mannheim (DE); Wilfried Lubisch, Heidelberg (DE); Gerd Steiner, Kirchheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/842,776

(22) Filed: Jul. 23, 2010

(65) Prior Publication Data

US 2011/0118232 A1    May 19, 2011

Related U.S. Application Data

(62) Division of application No. 11/628,658, filed as application No. PCT/EP2005/006000 on Jun. 3, 2005, now Pat. No. 7,786,105.

(30) Foreign Application Priority Data

Jun. 4, 2004 (DE) .......................... 10 2004 027 358

(51) Int. Cl.
C07D 401/12 (2006.01)
C07D 413/12 (2006.01)
C07D 417/12 (2006.01)
A61K 31/506 (2006.01)
A61P 25/36 (2006.01)

(52) U.S. Cl. ...................... 514/218; 540/575
(58) Field of Classification Search ............. 540/575; 514/218
See application file for complete search history.

(56) References Cited

U.S. PATENT DOCUMENTS

| 5,958,923 | A | 9/1999 | Hellendahl et al. |
| 6,342,604 | B1 | 1/2002 | Hellendahl et al. |
| 6,472,392 | B1 | 10/2002 | Starck et al. |
| 7,223,765 | B2 | 5/2007 | Bang-Andersen et al. |
| 2003/0232822 | A1 | 12/2003 | Bang-Andersen et al. |

FOREIGN PATENT DOCUMENTS

| JP | 10502659 | 2/1996 |
| JP | 10502915 | 2/1996 |
| JP | 2002504549 A | 2/2002 |
| JP | 2002507999 A | 3/2002 |
| JP | 2003519225 A | 6/2003 |
| JP | 2004501912 A | 1/2004 |
| WO | 9725324 | 7/1997 |
| WO | 99/43670 A1 | 9/1999 |

OTHER PUBLICATIONS

Benoit, et al., "Altered Feeding Responses in Mice with Targeted Disruption of the Dopamine-3 Receptor Gene," Behavioral Neuroscience 2003, vol. 117, No. 1, pp. 46-54.
Heidbreder, et al., "The Role of Central D3 Receptors in Drug Addiction: a Review of Pharmacological Evidence," Brain Research Reviews 2005, vol. 49, pp. 77-105.
Joyce, "Dopamine D3 Receptor as Therapeutic Target for Antipsychotic and Antiparkinsonian Drug," Pharmacology & Therapeutics, 2001, vol. 90, pp. 231-259.
Muhlbauer, et al., "Dopamine D3 receptors in the rat kidney role in physiology and pathophysiology," Acta. Physicol. Scand., 2000, vol. 168, pp. 219-223.
Rogoz, et al., "Anxiolytic-Like Effects of Preferential Dopamine D3 Receptor Agonists in an Animal Model," Polish Journal of Pharmacology, 2003, vol. 55, pp. 449-454.
Orjales, A., et al., New 3-benzisothiazolyl and 3-benzisoxazolylpiperazine derivatives with atypical antipsychotic binding profile, European Journal of Medicinal Chemistry, 37, (2002), pp. 721-730.

*Primary Examiner* — Bruck Kifle
(74) *Attorney, Agent, or Firm* — Lisa V. Mueller; Michael Best & Friedrich LLP

(57) ABSTRACT

The invention relates to compounds of formula (I) and the use of these compounds.

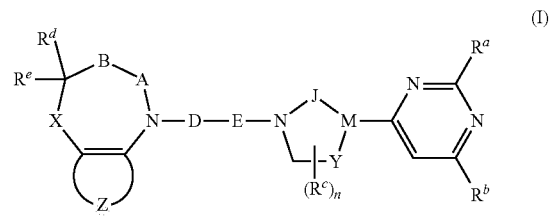

15 Claims, No Drawings

PYRIMIDINE COMPOUNDS AND USE THEREOF

CROSS-REFERENCE TO RELATED APPLICATIONS

This is a divisional of U.S. patent application Ser. No. 11/628,658, filed on Nov. 19, 2007, which is the U.S. National Stage of International Patent Application No. PCT/EP2005/006000, filed on Jun. 3, 2005, which claims priority to German Patent Application No. 10 2004 027 358.8, filed on Jun. 4, 2004, the contents of all of which are hereby incorporated by reference.

The present invention relates to novel pyrimidine compounds. These compounds have valuable therapeutic properties and are suitable in particular for the treatment of disorders which respond to modulation of the dopamine $D_3$ receptor.

Neurons receive their information inter alia via G protein-coupled receptors. There are numerous substances which exert their effect via these receptors. One of these is dopamine. Confirmed findings about the presence of dopamine and its physiological function as neurotransmitter have been published. Disturbances in the dopaminergic transmitter system result in disorders of the central nervous system which include, for example, schizophrenia, depression or Parkinson's disease. These and other disorders are treated with medicaments which interact with the dopamine receptors.

Until 1990, two subtypes of dopamine receptors were clearly defined pharmacologically, namely the $D_1$ and $D_2$ receptors. More recently, a third subtype has been found, namely the $D_3$ receptor, which appears to mediate some effects of antipsychotics and antiparkinsonian drugs (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-259 "The Dopamine $D_3$ Receptor as a Therapeutic Target for Antipsychotic and Antiparkinsonian Drugs").

Dopamine receptors are now divided into two families. Firstly the $D_2$ group consisting of $D_2$, $D_3$ and $D_4$ receptors, and secondly the $D_1$ group consisting of $D_1$ and $D_5$ receptors. Whereas $D_1$ and $D_2$ receptors are widespread, the expression of $D_3$ receptors by contrast appears to be regioselective. Thus, these receptors are preferentially found in the limbic system, the projecting regions of the mesolimbic dopamine system, especially in the nucleus accumbens, but also in other regions such as amygdala. Because of this comparatively regioselective expression, $D_3$ receptors are regarded as a target with few side effects, and it is assumed that a selective $D_3$ ligand ought to have the properties of known antipsychotics but not their dopamine $D_2$ receptor-mediated neurological side effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

Pyrimidine compounds having dopamine $D_3$ receptor affinity have been described in various forms in the prior art, for example in WO 96/02519, WO 96/02520, WO 96/02249, WO 96/02246, WO 99/02503, WO 00/42036, WO 00/42037, WO 00/42038. Some of these compounds have high affinities for the dopamine $D_3$ receptor. They are therefore proposed for the treatment of disorders of the central nervous system.

However, there is always a need to provide further compounds having dopamine $D_3$ receptor affinity, perhaps to improve the pharmacological binding profile, or because prior art compounds cause unwanted side effects, display poor cerebral availability or have only a low bioavailability. The invention is therefore based on the object of providing further compounds which act as selective dopamine $D_3$ receptor ligands.

This object is achieved by compounds which comply with the general formula I

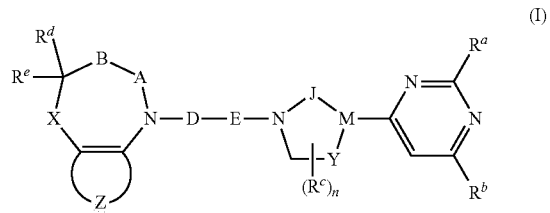

in which
A is a C=W or $CR^fR^g$ group;
B is a chemical bond or a $CR^hR^i$ group;
X is O, S, an N—$R^k$ group or a $CR^mR^n$ group;
D is C=O or a chemical bond;
E is a linear or branched 2 to 10 membered alkylene chain which may have as chain members 1 or 2 non-adjacent heteroatomic group(s) K which is selected from O, S, S(O), S(O)$_2$ and N—$R^p$, and which may comprise a carbonyl group and/or a cycloalkanediyl group and/or may have a double or triple bond;
W is oxygen or sulfur;
Z forms together with the C atoms to which it is bonded a fused 5-, 6- or 7-membered carbocycle or heterocycle which has 1, 2, 3 or 4 heteroatoms which are selected from N, O and S, where the fused carbocycle and the fused heterocycle may have 1 or 2 carbonyl groups as ring members and/or 1, 2, 3 or 4 substituents R which are selected from optionally substituted $C_1$-$C_6$-alkyl, CN, OR$^1$, NR$^2$R$^3$, NO$_2$, SR$^4$, SO$_2$R$^4$, SO$_2$NR$^2$R$^3$, CONR$^2$R$^3$, COOR$^5$, COR$^6$, $C_1$-$C_4$-haloalkoxy, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkyloxy and halogen and/or 2 substituents R may together form a chain X'-Alk'-X" in which X' and X" are independently of one another O or S, and Alk' is $C_1$-$C_4$-alkanediyl which optionally has 1, 2, 3 or 4 alkyl groups or halogen atoms as substituents;
J is CH$_2$, CH$_2$—CH$_2$ or CH$_2$—CH$_2$—CH$_2$;
M is CH or N;
Y is CH$_2$, CH$_2$—CH$_2$ or CH$_2$—CH$_2$—CH$_2$, or M-X together are CH=C or CH$_2$—CH=C;
n is 0 or 1;
$R^a$, $R^b$ are independently of one another selected from optionally substituted $C_1$-$C_6$-alkyl, $C_2$-$C_6$-alkenyl, $C_2$-$C_6$-alkynyl, $C_3$-$C_6$-cycloalkyl, $C_4$-$C_{10}$-bicycloalkyl and $C_6$-$C_{10}$-tricycloalkyl, where the last three groups mentioned may optionally be substituted by halogen or $C_1$-$C_4$-alkyl, or halogen, CN, OR$^1$, NR$^2$R$^3$, NO$_2$, SR$^4$, SO$_2$R$^5$, CONR$^2$R$^3$, SO$_2$NR$^2$R$^3$, COOR$^5$, COR$^6$, O—COR$^6$, 5- or 6-membered heterocyclyl having 1, 2 or 3 heteroatoms selected from O, S and N, and phenyl, where phenyl and heterocyclyl may optionally have 1, 2 or 3 substituents which are selected independently of one another from $C_1$-$C_4$-alkyl, $C_1$-$C_4$-alkoxy, NR$^2$R$^3$, CN, $C_1$-$C_2$-fluoroalkyl and halogen;
$R^c$ is $C_1$-$C_4$-alkyl;
$R^d$, $R^e$ are independently of one another selected from hydrogen, halogen, optionally substituted $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_3$-$C_6$-cycloalkyloxy, $C_3$-$C_6$-cycloalkyl-$C_1$-$C_4$-alkyloxy and optionally substituted phenyl, where $CR^dR^e$ may together be C=O, and the radicals $R^d$, $R^e$ may together form a chain X'-Alk-X" in which X and X" are independently of one another O or S, and Alk is $C_2$-$C_4$-alkanediyl which optionally has 1, 2 3 or 4 alkyl groups or halogen atoms as substituents;

$R^f$, $R^g$ are independently of one another hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl, or the radicals $R^f$, $R^g$ may together form a chain X'-Alk-X" in which Alk, X' and X" have the aforementioned meanings;

$R^h$, $R^i$ are independently of one another hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl;

$R^k$, $R^p$ are independently of one another hydrogen, $C_1$-$C_4$-alkyl, $C_1$-$C_6$-alkoxy, $C_1$-$C_6$-alkoxyalkyl, $C_1$-$C_6$-alkylcarbonyl, $C_1$-$C_6$-alkoxycarbonyl, phenylalkyl, phenylcarbonyl, phenoxycarbonyl, where phenyl in the last three groups mentioned may have 1, 2 or 3 substituents which are selected from $C_1$-$C_4$-alkyl, $C_1$-$C_4$-alkoxy, $NR^2R^3$, CN, $C_1$-$C_2$-fluoroalkyl and halogen;

$R^m$, $R^n$ are independently of one another hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl; and in the case where X is $CR^mR^n$ or N—$R^k$, one of the radicals $R^d$ or $R^e$ may together with one of the radicals $R^m$, $R^n$ or $R^k$ also be a π bond;

$R^1$, $R^2$, $R^3$, $R^4$, $R^5$ and $R^6$ are independently of one another H, optionally substituted $C_1$-$C_6$-alkyl or optionally substituted phenyl, where $R^3$ may also be a group $COR^7$, where $R^7$ is hydrogen, optionally substituted $C_1$-$C_4$-alkyl or optionally substituted phenyl, where $R^2$ with $R^3$ may also form together with the nitrogen atom to which they are bonded a 5- or 6-membered, saturated or unsaturated heterocycle which may have a further heteroatom selected from O, S and $NR^8$ as ring member, where $R^8$ is hydrogen or $C_1$-$C_4$-alkyl, and the physiologically acceptable acid addition salts of these compounds.

The present invention therefore relates to the compounds of the general formula I and to the physiologically tolerated acid addition salts of the compounds I.

The present invention also relates to the use of the compounds of the general formula I and of the physiologically tolerated acid addition salts of the compounds I for producing a pharmaceutical composition for the treatment of conditions which respond to influencing by dopamine $D_3$ receptor antagonists or agonists.

Conditions which respond to influencing by dopamine $D_3$ receptor antagonists or agonists include in particular disorders and conditions of the central nervous system, especially affective disorders, neurotic disorders, stress disorders and somatoform disorders and psychoses, specifically schizophrenia and depression and in addition renal function disorders, especially renal function disorders caused by diabetes mellitus (see WO 00/67847).

The aforementioned indications are treated by using according to the invention at least one compound of the general formula I or a physiologically tolerated acid addition salt of a compound I. If the compounds of the formula I have one or more centers of asymmetry or form tautomers, it is also possible to employ mixtures of enantiomers, especially racemates, mixtures of diastereomers, mixtures of tautomers, but preferably the respective substantially pure enantiomers, diastereomers and tautomers.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids such as methanesulfonic acid, aromatic sulfonic acids such as benzenesulfonic acid and toluenesulfonic acid, oxalic acid, maleic acid, fumaric acid, lactic acid, tartaric acid, adipic acid and benzoic acid. Further acids which can be used are described in Fortschritte der Arzneimittelforschung, volume 10, pages 224 et seq., Birkhäuser Verlag, Basel and Stuttgart, 1966.

Halogen here and hereinafter is fluorine, chlorine, bromine or iodine.

$C_n$-$C_m$-Alkyl (also in radicals such as alkoxy, alkoxyalkyl, alkylthio, alkylamino, dialkylamino, alkylcarbonyl, etc.) means a straight-chain or branched alkyl group having n to m carbon atoms, e.g. 1 to 6 and especially 1 to 4 carbon atoms. Examples of an alkyl group are methyl, ethyl, n-propyl, isopropyl, n-butyl, 2-butyl, isobutyl, tert-butyl, n-pentyl, 2-pentyl, neopentyl, n-hexyl and the like.

The expression "optionally substituted $C_n$-$C_m$-alkyl" stands for an alkyl radical which has n to m C atoms, which may be partially or completely substituted by halogen, in particular by chlorine or fluorine, and which may have one or more, e.g. 1, 2 or 3, substituents different from halogen which are selected from CN, $C_3$-$C_7$-cycloalkyl, $C_3$-$C_7$-heterocycloalkyl, optionally substituted phenyl, $OR^{11}$, $COOR^{11}$, $NR^{12}R^{13}$, $SO_2NR^{12}R^{13}$, $CONR^{12}R^{13}$, O—$CONR^{12}R^{13}$, S—$R^{14}$, $SOR^{15}$, $SO_2R^{15}$, $OCOR^{16}$ and $COR^{16}$. In these, $R^{11}$ has the meaning indicated for $R^1$, $R^{12}$ the meaning indicated for $R^2$, $R^{13}$ the meaning indicated for $R^3$, $R^{14}$ the meaning indicated for $R^4$, $R^{15}$ the meaning indicated for $R^5$ and $R^{16}$ the meaning indicated for $R^6$. In particular, $R^{11}$-$R^{16}$ are hydrogen, $C_1$-$C_4$-alkyl, $C_1$-$C_4$-haloalkyl, $C_3$-$C_7$-cycloalkyl, optionally substituted benzyl or optionally substituted phenyl.

Preferred substituents on alkyl are selected from OH, $C_1$-$C_4$-alkoxy, halogen, $C_3$-$C_7$-cycloalkyl and optionally substituted phenyl. In the case of OH, $C_1$-$C_4$-alkoxy, $C_3$-$C_7$-cycloalkyl and phenyl there is in particular only one substituent. Radicals of these types are also referred to hereinafter as $C_1$-$C_4$-alkoxy-$C_1$-$C_6$-alkyl such as methoxymethyl, 1- or 2-methoxyethyl, 1-methoxy-1-methylethyl or 2-methoxy-1-methylethyl, 1-, 2- or 3-methoxypropyl, ethoxymethyl, 1- or 2-ethoxyethyl, hydroxy-$C_1$-$C_6$-alkyl, 1-hydroxymethyl, 1- or 2-hydroxyethyl, 1-hydroxy-1-methylethyl, 1-, 2- or 3-hydroxypropyl etc., $C_3$-$C_6$-cycloalkyl-$C_1$-$C_6$-alkyl such as cyclopropylmethyl, cyclohexylmethyl or phenyl-$C_1$-$C_6$-alkyl. In the case of halogen substituents, these radicals are also referred to as haloalkyl.

$C_1$-$C_6$-Haloalkyl (also in radicals such as $C_1$-$C_6$-haloalkoxy) stands for an alkyl group which has 1 to 6 and, in particular 1 to 4 C atoms as defined above, in which all or some, e.g. 1, 2, 3, 4 or 5, of the hydrogen atoms are replaced by halogen atoms, in particular by chlorine or fluorine. Preferred haloalkyl is $C_1$-$C_2$-fluoroalkyl or $C_1$-$C_2$-fluoro-chloroalkyl, in particular $CF_3$, $CHF_2$, $CF_2Cl$, $CH_2F$, $CH_2CF_3$.

$C_3$-$C_{10}$-Cycloalkyl, also in radicals such as cycloalkylalkyl, cycloalkylcarbonyl and cycloalkylcarbonylalkyl, stands for a cycloaliphatic radical having 3 to 10 and preferably 3 to 6 C atoms, such as cyclopropyl, cyclobutyl, cyclopentyl, cyclohexyl, cycloheptyl and cyclooctyl.

$C_3$-$C_{10}$-Heterocycloalkyl, also in radicals such as heterocycloalkylalkyl, heterocycloalkylcarbonyl and heterocycloalkylcarbonylalkyl, stands for a saturated heterocyclic radical having ring members, where 1, 2 or 3 ring members are a heteroatom selected from N, O and S, such as oxiranyl, oxetanyl, aziranyl, azetanyl, tetrahydrofurfuryl, tetrahydrothienyl, pyrrolidinyl, pyrazolinyl, imidazolinyl, piperidinyl, piperazinyl or morpholinyl.

$C_4$-$C_{10}$-Bicycloalkyl stands for a bicycloaliphatic radical having 4 to 10 C atoms as in bicyclo[2.1.0]pentyl, bicyclo[2.1.1]hexyl, bicyclo[3.1.0]hexyl, bicyclo[2.2.1]heptanyl, bicyclo[3.2.0]heptanyl, bicyclo[2.2.2]octanyl, bicyclo[3.2.1]octanyl, bicyclo[3.3.1]nonyl and bicyclo[4.4.0]decyl.

$C_6$-$C_{10}$-Tricycloalkyl stands for a tricycloaliphatic radical having 6 to 10 C atoms as in adamantyl.

$C_2$-$C_6$-Alkenyl stands for a monounsaturated linear or branched hydrocarbon, radical having 2, 3, 4, 5 or 6 C atoms, e.g. for vinyl, allyl (2-propen-1-yl), 1-propen-1-yl, 2-propen-2-yl, methallyl (2-methylprop-2-en-1-yl) and the like. $C_3$-$C_4$-Alkenyl is in particular allyl, 1-methylprop-2-en-1-yl, 2-buten-1-yl, 3-buten-1-yl or methallyl.

$C_2$-$C_6$-Haloalkenyl stands for an alkenyl group as defined above, in which all or some, e.g. 1, 2, 3, 4 or 5, of the hydrogen atoms are replaced by halogen atoms, in particular by chlorine or fluorine.

$C_2$-$C_6$-Alkynyl stands for a hydrocarbon radical having 2, 3, 4, 5 or 6 C atoms and having a triple bond, e.g. for propargyl (2-propyn-1-yl), 1-methylprop-2-yn-1-yl, 2-butyn-1-yl, 3-butyn-1-yl, 2-pentyn-1-yl, 1-pentyn-3-yl, etc.

$C_2$-$C_6$-Haloalkynyl stands for an alkynyl group as defined above, in which all or some, e.g. 1, 2, 3, 4 or 5, of the hydrogen atoms are replaced by halogen atoms, in particular by chlorine or fluorine.

Phenyl-$C_1$-$C_4$-alkyl stands for a $C_1$-$C_4$-alkyl radical as defined above, in which a hydrogen atom is replaced by a phenyl radical, as in benzyl or 2-phenylethyl.

Optionally substituted phenyl stands for phenyl that optionally has one or more, e.g. 1, 2 or 3, of the following substituents: halogen, nitro, cyano, optionally substituted $C_1$-$C_4$-alkyl, $C_2$-$C_6$-alkenyl, $C_2$-$C_6$-alkynyl, $C_3$-$C_6$-cycloalkyl, $C_1$-$C_4$-haloalkyl, $C_1$-$C_4$-alkoxy, $C_1$-$C_4$-alkylsulfonylamino, $OR^{21}$, $COOR^{21}$, $NR^{22}R^{23}$, $SO_2NR^{22}R^{23}$, $CONR^{22}R^{23}$, $O-CONR^{22}R^{23}$, $S-R^{24}$, $SOR^{25}$, $SO_2R^{25}$, $OCOR^{26}$ and $COR^{26}$. Examples of suitable substituents on phenyl are in particular halogen, $C_1$-$C_4$-alkyl, $C_2$-$C_6$-alkenyl, $C_2$-$C_6$-alkynyl, $C_3$-$C_6$-cycloalkyl, $C_1$-$C_4$-haloalkyl, $C_1$-$C_4$-alkoxy, $C_1$-$C_4$-alkoxy-$C_1$-$C_4$-alkyl, hydroxy-$C_1$-$C_4$-alkyl, hydroxy, nitro, $NH_2$, cyano, COOH, $C_1$-$C_4$-alkoxycarbonyl, $C_1$-$C_4$-alkylcarbonyl, $C_1$-$C_4$-alkylamino, di($C_1$-$C_4$-alkyl) amino, $C_1$-$C_4$-alkylsulfonyl, $C_1$-$C_4$-alkylsulfonylamino and/or $C_1$-$C_4$-alkylaminosulfonyl. In these, $R^{21}$ has the meaning indicated for $R^1$, $R^{22}$ the meaning indicated for $R^2$, $R^{23}$ the meaning indicated for $R^3$, $R^{24}$ the meaning indicated for $R^4$, $R^{25}$ the meaning indicated for $R^5$, and $R^{26}$ the meaning indicated for $R^6$. In particular, $R^{21}$-$R^{26}$ are hydrogen. $C_1$-$C_4$-Alkyl, $C_1$-$C_4$-haloalkyl, $C_3$-$C_7$-cycloalkyl, optionally substituted benzyl or optionally substituted phenyl.

The term "alkylene" comprises in principle straight-chain or branched radicals having preferably 2 to 10 and particularly preferably 3 to 8 carbon atoms such as prop-1,2-ylene, prop-1,3-ylene, but-1,2-ylene, but-1,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, hex-1,3-ylene, hex-2,4-ylene, hex-1,4-ylene, hex-1,5-ylene, hex-1,6-ylene and the like. $C_0$-Alkylene stands for a single bond, $C_1$-alkylene for methylene and $C_2$-alkylene for 1,1-ethylene or 1,2-ethylene.

The term 3 to 8 membered heterocyclyl comprises saturated (=heterocycloalkyl), partially unsaturated heterocyclic radicals and aromatic heterocycles (heteroaryl) of ring size 3, 4, 5, 6, 7 and 8, in particular of ring size 5 or 6, having 1, 2 or 3 heteroatoms as ring members. The heteroatoms in this case are selected from O, S and N.

Examples of saturated 3- to 8-membered heterocyclyl are oxiranyl, oxetanyl, aziranyl, piperidinyl, piperazinyl, morpholinyl, pyrrolidinyl, oxazolidinyl, tetrahydrofuryl, dioxolanyl, dioxanyl, hexahydroazepinyl, hexyhydrooxepinyl, and hexahydrothiepinyl.

Examples of partially unsaturated 3- to 8-membered heterocyclyl are di- and tetrahydropyridinyl, pyrrolinyl, oxazolinyl, dihydrofuryl, tetrahydroazepinyl, tetrahydrooxepinyl, and tetrahydrothiepinyl.

Examples of 5-membered heteroaromatic radicals (=5-membered heteroaryl) are those having 1, 2, 3 or 4 heteroatoms as ring members which are selected independently of one another from O, N and S, e.g. pyrrole, thiophene, furan, oxazole, isoxazole, thiazole, isothiazole, imidazole, 1,2,3-thiadiazole, 1,2,4-thiadiazole, 1,3,4-thiadiazole, 1,2,3-triazole, 1,2,4-triazole, 1,3,4-triazole, tetrazole. Examples of 6-membered heteroaromatic radicals (=6-membered heteroaryl) having 1 or 2 nitrogen atoms as ring members are in particular 2-, 3- or 4-pyridinyl, 2-, 4- or 5-pyrimidinyl, 2- or 3-pyrazinyl and 3- or 4-pyridazinyl.

The group Z forms according to the invention with the C atoms to which it is bonded a 5-, 6- or 7-membered carbocycle or a 5-, 6- or 7-membered heterocycle, each of which may be substituted in the manner described above. Besides the double bond located between the bridge head atoms, both the carbocycle and the heterocycle may have one or two further double bonds or form an aromatic ring. Suitable fused carbocycles are, besides cyclopentene, cyclohexene and cycloheptene, also cyclopentadiene, cyclohexa-1,3- and 1,4-diene, cyclohepta-1,3- and 1,4-diene and, in particular, phenyl. Suitable 5-, 6- or 7-membered heterocyclic fused rings are in particular the aforementioned heterocyclic groups which have at least 2 adjacent C atoms as ring members. Examples of these are pyrrole, 2,3-dihydropyrrole, 2,5-dihydropyrrole, thiophene, 2,3-dihydrothiophene, 2,5-dihydrothiophene, furan, 2,3-dihydrofuran, 2,5-dihydrofuran, pyridine, 1,2-, 1,4-, 3,4- and 2,3-dihydropyridine, 1,2,3,4- and 1,2,3,6-tetrahydropyridine, pyrimidine, piperazine, piperazine, di- and tetrahydroazepines, di- and tetrahydro-1,3- and 1,4-diazepines and the like.

In group E, the two binding sites of the alkylene chain are usually not on the same C atom but form, optionally together with the heteroatomic group K, a chain which has at least two, preferably at least three, and in particular at least four, members and which, if D is a bond, separates the nitrogen atom linked to A from the nitrogen atom of the nitrogen heterocycle or, if D is a carbonyl group, separates the carbonyl group from the nitrogen atom of the nitrogen heterocycle to which E is bonded by at least 3, preferably by at least 4 and in particular by at least 5 bonds from one another. If E has no heteroatomic group K, then E preferably comprises 4 to 10 carbon atoms, in particular 4 to 8 carbon atoms and particularly preferably 4 to 6 carbon atoms as chain members. If E has a heteroatomic group K, then E comprises besides these groups in particular 2 to 8 carbon atoms and specifically 3 to 5 carbon atoms as chain members. It is additionally possible for the saturated C—C bonds in E to be replaced by unsaturated bonds (alkenylene; alkynylene). Thus, possible results are straight-chain or branched unsaturated radicals in which the number and disposition of the carbon atoms corresponds to that of the aforementioned alkylene radicals, but where one or more single bonds are replaced by corresponding unsaturated double or triple bonds. E may additionally comprise a cycloalkanediyl radical, preferably a $C_3$-$C_7$-cycloalkanediyl radical, in particular a $C_4$-$C_7$-cycloalkane-1,2-, -1,3- or 1,4-diyl radical, e.g. cyclopropane-1,2-diyl, cyclobutane-1,2- or 1,3-diyl, cyclopentane-1,2- or -1,3-diyl, cyclohexane-1,2-, 1,3- or -1,4-diyl radical, or a cycloheptane-1,2-, -1,3- or 1,4-diyl radical. This cycloalkanediyl radical is a constituent of the chain E. In other words, the chain E is formed by part of the cycloalkanediyl radical with the remaining chain members, the chain length being determined by the smaller part of the cycloalkanediyl radical.

If the alkylene group in E comprises at least one heteroatom, a heteroatomic group K, this can be disposed at any site in the alkylene chain. The heteroatom is preferably not bonded to the nitrogen atom. A carbonyl group is preferably bonded to the nitrogen atom adjacent to A.

Examples of suitable groups E are:
$(CH_2)_k$ with k=2, 3, 4, 5, 6, 7, 8, 9 or 10, preferably 3, 4, 5 or 6 and specifically 3 or 4;
$CH(CH_3)(CH_2)_l$ with l=1, 2, 3, 4, 5, 6, 7, 8 or 9, in particular 2, 3, 4 or 5 and specifically 2 or 3;
$CH_2CH(CH_3)(CH_2)_{k'}$ with k'=0, 1, 2, 3, 4, 5, 6, 7 or 8, cis- and trans-$CH_2$—CH=$CHCH_2$, cis- and trans-$CH_2$—$C(CH_3)$=CH—$CH_2$, cis- and trans-$CH_2CH_2CH$=$CHCH_2$, cis- and trans-$CH_2CH_2C(CH_3)$=$CHCH_2$, $CH_2C$(=$CH_2$)$CH_2$, $CH_2CH_2CH(CH_3)CH_2$,

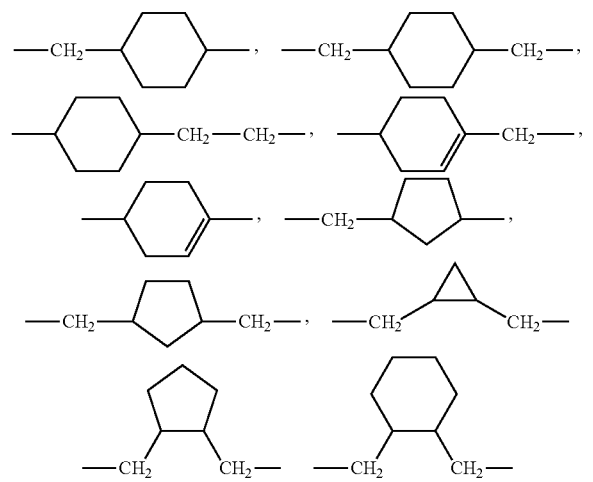

$CH_2$—O—$CH_2$—$CH_2$, $CH_2$—O—$CH_2$—$CH_2$—$CH_2$ and —$CH_2$—$CH_2$—O—$CH_2$—$CH_2$—.

With a view to the use of the compounds of the invention as dopamine $D_3$ receptor ligands, particularly preferred compounds I are those in which E in formula I is $C_3$-$C_{10}$-alkylene, in particular $C_3$-$C_8$-alkylene and specifically $C_3$-$C_6$-alkylene, which may have a double bond. E is in particular a group $(CH_2)_k$ in which k has the aforementioned meanings. Particularly preferred group E are additionally cis- and trans-$CH_2$—CH=CH—$CH_2$, cis- and trans-$CH_2$—$C(CH_3)$=CH—$CH_2$, $CHCH_3$—$CH_2$—$CH_2$—$CH_2$ and $CH_2$—$CHCH_3$—$CH_2$—$CH_2$.

If A is C=W, then D is preferably a chemical bond. W is in particular oxygen. If A is $CR^fR^g$, then D is preferably a carbonyl group. $R^f$ and $R^g$ are, independently of one another, in particular hydrogen or $C_1$-$C_4$-alkyl, specifically methyl. In particular, at least one and specifically both of the radicals $R^f$ and $R^g$ is hydrogen.

X in formula I is in particular O or a group $CR^mR^n$ in which $R^m$ and $R^n$ have the aforementioned meanings, in particular hydrogen or $C_1$-$C_4$-alkyl, specifically methyl, and particularly preferably hydrogen. X is particularly preferably $CH_2$.

A preferred embodiment of the invention relates to compounds of the general formula I in which Z together with the C atoms to which it is bonded is a fused 6-membered carbocycle which is unsubstituted or may have 1, 2, 3 or 4, in particular 1 or 2, of the aforementioned substituents R. In particular, Z forms together with the C atoms to which it is bonded an optionally substituted phenyl ring. In particular, the phenyl ring is unsubstituted or has one of the aforementioned substituents R. The latter is preferably bonded to the carbon atoms which is adjacent to the bridge head atoms and in particular to the carbon atom which is adjacent to the bridge head atom which is bonded to the group X. Preferred compounds are also those in which Z together with the C atoms to which it is bonded forms an optionally substituted cyclohexene ring which optionally has a carbonyl group as ring member, e.g. a cyclohex-2-enone ring.

Preferred substituents R on Z are $C_1$-$C_4$-alkyl, specifically methyl, ethyl, n-propyl, n-butyl and tert-butyl, OH, halogen, in particular F, Cl or Br, $C_1$-$C_4$-alkoxy, specifically methoxy, $C_1$-$C_4$-alkylamino, di-$C_1$-$C_4$-alkylamino, specifically $N(CH_3)_2$, $C_1$-$C_4$-alkylcarbonyl, specifically acetyl, $C_1$-$C_4$-alkoxycarbonyl, specifically methoxycarbonyl, $C_1$-$C_4$-alkylsulfonyl, specifically methylsulfonyl, $C_1$-$C_4$-haloalkyl, specifically trifluoromethyl, $C_1$-$C_4$-haloalkoxy, specifically trifluoromethoxy and difluoromethoxy, CN and $C(O)NH_2$, in particular $C_1$-$C_4$-alkyl, OH, halogen and $C_1$-$C_4$-alkoxy, specifically OH, methoxy, F, Cl, Br, $CF_3$ and $OCF_3$. It is also preferred for 2 groups R bonded to adjacent C atoms to be O-Alk'-O in which Alk' is $CH_2$, $CF_2$, $CH_2$—$CH_2$ or $C(CH_3)_2$.

In relation to their property as selective dopamine $D_3$ receptor ligands, preferred compounds of the general formula I are additionally those in which M is a nitrogen atom. J is in particular $CH_2$—$CH_2$. Y is in particular $CH_2$ or $CH_2$—$CH_2$. In a particularly preferred embodiment, J in formula I is $CH_2$—$CH_2$ and Y is $CH_2$. M is then in particular N.

In relation to their property as selective dopamine $D_3$ receptor ligands, preferred compounds of the general formula I are additionally those in which $R^a$ and $R^b$ are independently of one another $C_1$-$C_6$-alkyl, $C_1$-$C_6$-haloalkyl, $C_2$-$C_6$-alkenyl, $C_3$-$C_6$-cycloalkyl, $C_1$-$C_6$-alkoxy-$C_1$-$C_4$-alkyl or $C_3$-$C_6$-cycloalkyl-$C_1$-$C_4$-alkyl. $R^a$ is in particular $C_1$-$C_6$-alkyl, particularly preferably branched $C_3$-$C_6$-alkyl and specifically tert-butyl. $R^b$ is selected in particular from $C_1$-$C_6$-alkyl, $C_3$-$C_6$-cycloalkyl and $C_1$-$C_2$-fluoroalkyl, particularly preferably n-propyl, trifluoromethyl, cyclopropyl or cyclobutyl.

A preferred embodiment of the invention relates to compounds of the general formula I in which B is a chemical bond.

In another preferred embodiment of the invention, B is a group $CR^hR^i$ in which $R^h$, $R^i$ are independently of one another in particular hydrogen or $C_1$-$C_4$-alkyl, specifically methyl. In particular, at least one and specifically both radicals $R^h$ and $R^i$ is hydrogen.

The variables $R^d$ and $R^e$ are independently of one another in particular hydrogen or $C_1$-$C_4$-alkyl, specifically methyl and particularly preferably both hydrogen.

In particular, the group of the formula

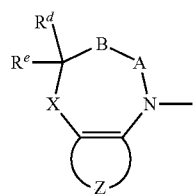

is one of the radicals a to e indicated below:

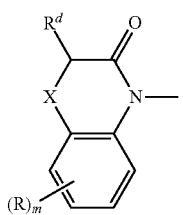

(a)

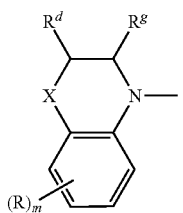

(b)

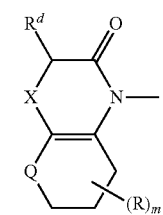

(c)

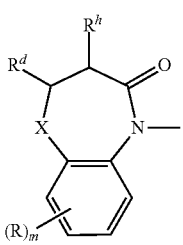

(d)

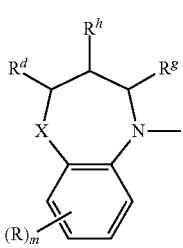

(e)

in which X, R, $R^d$, $R^g$ and $R^h$ have the aforementioned meanings, m is 0, 1, 2 or 3, in particular m is 0 or 1, and Q is $CH_2$ or a carbonyl group.

Accordingly, preferred embodiments of the invention are the compounds of the general formula Ia to Ie indicated below,

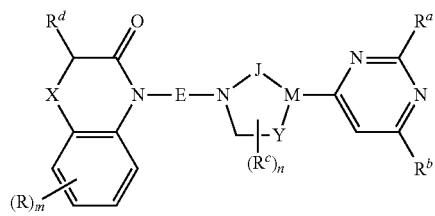

(Ia)

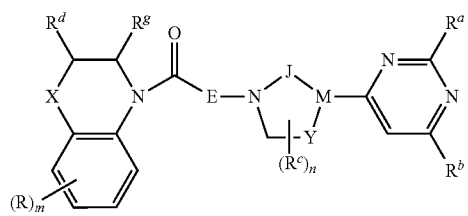

(Ib)

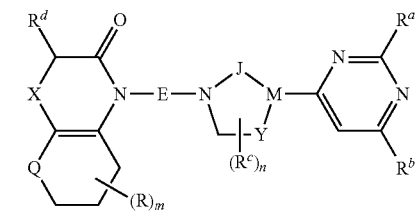

(Ic)

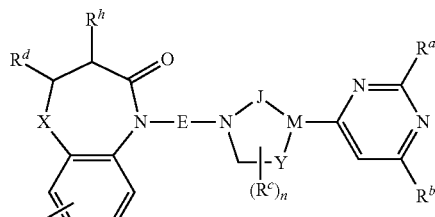

(Id)

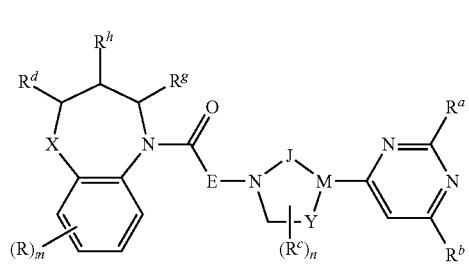

(Ie)

in which n, m Q, X, E, J, M, R, $R^a$, $R^b$, $R^c$, $R^d$, $R^g$ and $R^h$ have the aforementioned meanings and in particular jointly have the meanings mentioned as preferred.

Among the compounds Ia, particularly preferred compounds have the following formulae Ia.1 to Ia.8:

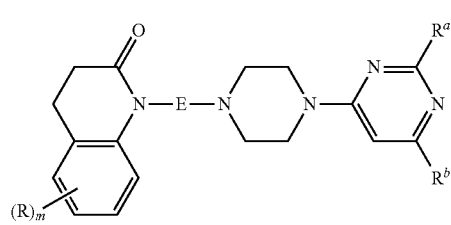

(Ia.1)

Examples thereof are the compounds of the formulae Ia.1, Ia.2, Ia.3, Ia.4, Ia.5, Ia.6, Ia.7 and Ia.8 in which E is butane-1,4-diyl, and m, R, $R^a$ and $R^b$ each jointly have the meanings indicated in one of the lines of table A.

Among the compounds Ib, particularly preferred compounds have the following formulae Ib.1, Ib.2, Ib.3 and Ib.4:

in which m, E, R, $R^a$ and $R^b$ have the aforementioned meanings and in particular jointly have the meanings mentioned as preferred.

Examples thereof are the compounds of the formulae Ib.1, Ib.2, Ib.3 and Ib.4 in which E is butane-1,4-diyl, and m, R, $R^a$ and $R^b$ each jointly have the meanings indicated in one of the lines of table A.

Among the compounds Ic, particularly preferred compounds have the following formulae Ic.1 to Ic.4:

in which m, E, R, $R^a$ and $R^b$ have the aforementioned meanings and in particular jointly have the meanings mentioned as preferred.

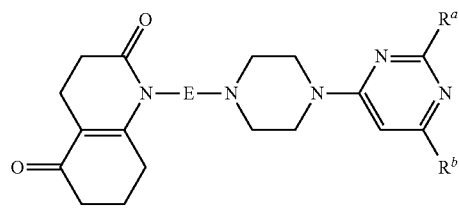
(Ic.2)

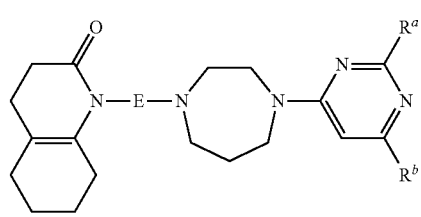
(Ic.3)

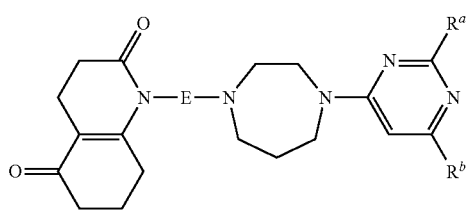
(Ic.4)

in which E, $R^a$ and $R^b$ have the aforementioned meanings and in particular jointly have the meanings mentioned as preferred.

Examples thereof are the compounds of the formulae Ic.1, Ic.2, Ic.3 and Ic.4 in which E is butane-1,4-diyl, and $R^a$ and $R^b$ each jointly have the meanings indicated in one of the lines 1 to 6 of table A.

Among the compounds Id, particularly preferred compounds have the following formulae Id.1 to Id.6:

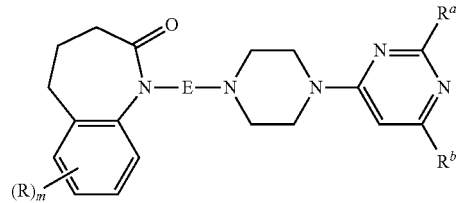
(Id.1)

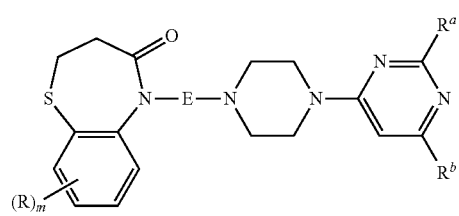
(Id.2)

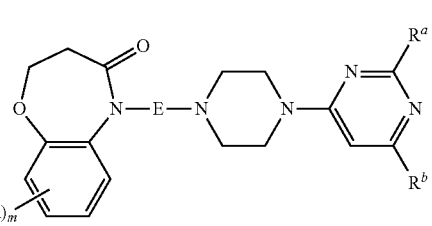
(Id.3)

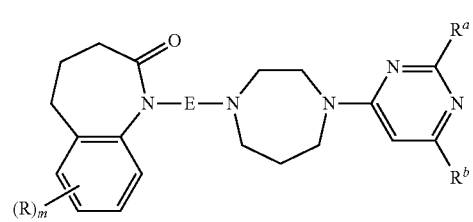
(Id.4)

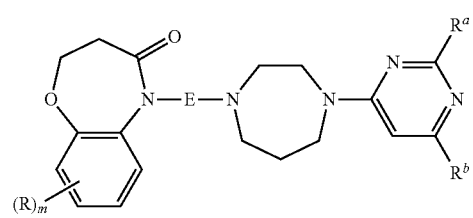
(Id.5)

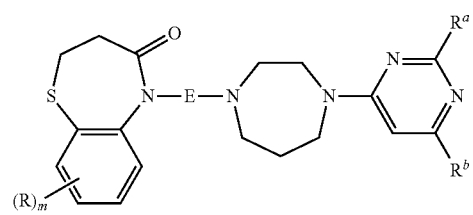
(Id.6)

in which m, E, R, $R^a$ and $R^b$ have the aforementioned meanings and in particular jointly have the meanings mentioned as preferred.

Examples thereof are the compounds of the formulae Id.1, Id.2, Id.3, Id.4, Id.5 and Id.6, in which E is butane-1,4-diyl, and m, R, $R^a$ and $R^b$ each jointly have the meanings indicated in one of the lines of table A.

Among the compounds Ie, particularly preferred compounds have the following formulae Ie.1 to Ie.6:

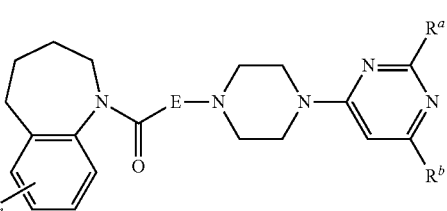
(Ie.1)

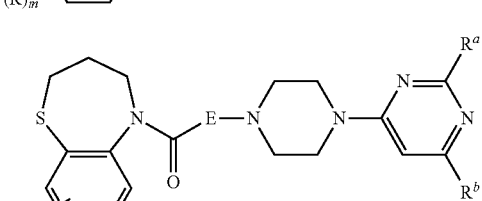
(Ie.2)

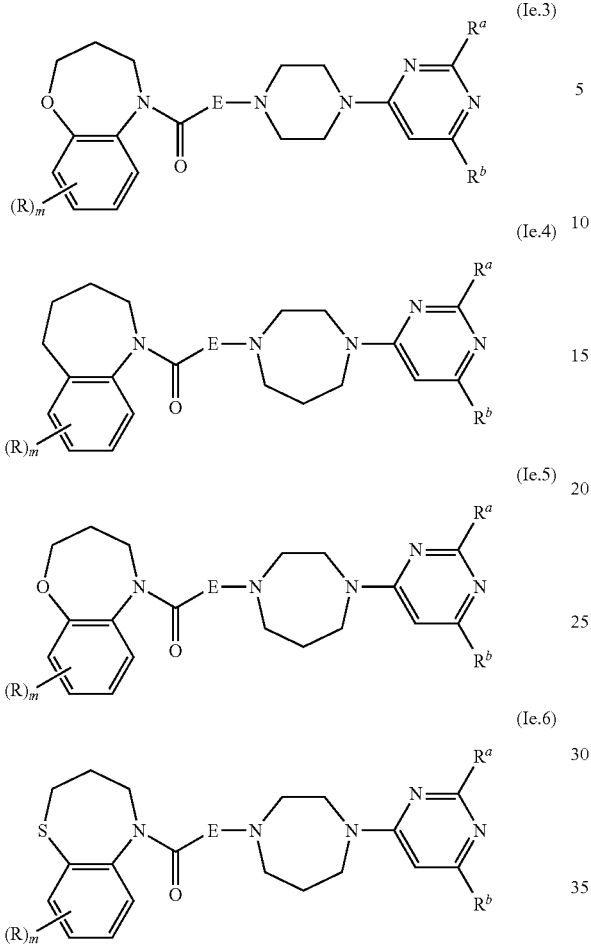

in which m, E, R, R$^a$ and R$^b$ have the aforementioned meanings and in particular jointly have the meanings mentioned as preferred.

Examples thereof are the compounds of the formulae Ie.1, Ie.2, Ie.3, Ie.4, Ie.5 and Ie.6, in which E is butane-1,4-diyl, and m, R, R$^a$ and R$^b$ each jointly have the meanings indicated in one of the lines of table A.

TABLE A

| No. | m | R | R$^a$ | R$^b$ |
|---|---|---|---|---|
| 1 | 0 | — | tert-Butyl | CF$_3$ |
| 2 | 0 | — | tert-Butyl | CHF$_2$ |
| 3 | 0 | — | tert-Butyl | n-Propyl |
| 4 | 0 | — | tert-Butyl | tert-Butyl |
| 5 | 0 | — | tert-Butyl | Cyclopropyl |
| 6 | 0 | — | tert-Butyl | Cyclopentyl |
| 7 | 1 | α-Cl | tert-Butyl | CF$_3$ |
| 8 | 1 | α-Cl | tert-Butyl | CHF$_2$ |
| 9 | 1 | α-Cl | tert-Butyl | n-Propyl |
| 10 | 1 | α-Cl | tert-Butyl | tert-Butyl |
| 11 | 1 | α-Cl | tert-Butyl | Cyclopropyl |
| 12 | 1 | α-Cl | tert-Butyl | Cyclopentyl |
| 13 | 1 | β-Cl | tert-Butyl | CF$_3$ |
| 14 | 1 | β-Cl | tert-Butyl | CHF$_2$ |
| 15 | 1 | β-Cl | tert-Butyl | n-Propyl |
| 16 | 1 | β-Cl | tert-Butyl | tert-Butyl |
| 17 | 1 | β-Cl | tert-Butyl | Cyclopropyl |
| 18 | 1 | β-Cl | tert-Butyl | Cyclopentyl |
| 19 | 1 | γ-Cl | tert-Butyl | CF$_3$ |
| 20 | 1 | γ-Cl | tert-Butyl | CHF$_2$ |
| 21 | 1 | γ-Cl | tert-Butyl | n-Propyl |
| 22 | 1 | γ-Cl | tert-Butyl | tert-Butyl |
| 23 | 1 | γ-Cl | tert-Butyl | Cyclopropyl |
| 24 | 1 | γ-Cl | tert-Butyl | Cyclopentyl |
| 25 | 1 | δ-Cl | tert-Butyl | CF$_3$ |
| 26 | 1 | δ-Cl | tert-Butyl | CHF$_2$ |
| 27 | 1 | δ-Cl | tert-Butyl | n-Propyl |
| 28 | 1 | δ-Cl | tert-Butyl | tert-Butyl |
| 29 | 1 | δ-Cl | tert-Butyl | Cyclopropyl |
| 30 | 1 | δ-Cl | tert-Butyl | Cyclopentyl |
| 31 | 1 | α-OH | tert-Butyl | CF$_3$ |
| 32 | 1 | α-OH | tert-Butyl | CHF$_2$ |
| 33 | 1 | α-OH | tert-Butyl | n-Propyl |
| 34 | 1 | α-OH | tert-Butyl | tert-Butyl |
| 35 | 1 | α-OH | tert-Butyl | Cyclopropyl |
| 36 | 1 | α-OH | tert-Butyl | Cyclopentyl |
| 37 | 1 | β-OH | tert-Butyl | CF$_3$ |
| 38 | 1 | β-OH | tert-Butyl | CHF$_2$ |
| 39 | 1 | β-OH | tert-Butyl | n-Propyl |
| 40 | 1 | β-OH | tert-Butyl | tert-Butyl |
| 41 | 1 | β-OH | tert-Butyl | Cyclopropyl |
| 42 | 1 | β-OH | tert-Butyl | Cyclopentyl |
| 43 | 1 | γ-OH | tert-Butyl | CF$_3$ |
| 44 | 1 | γ-OH | tert-Butyl | CHF$_2$ |
| 45 | 1 | γ-OH | tert-Butyl | n-Propyl |
| 46 | 1 | γ-OH | tert-Butyl | tert-Butyl |
| 47 | 1 | γ-OH | tert-Butyl | Cyclopropyl |
| 48 | 1 | γ-OH | tert-Butyl | Cyclopentyl |
| 49 | 1 | δ-OH | tert-Butyl | CF$_3$ |
| 50 | 1 | δ-OH | tert-Butyl | CHF$_2$ |
| 51 | 1 | δ-OH | tert-Butyl | n-Propyl |
| 52 | 1 | δ-OH | tert-Butyl | tert-Butyl |
| 53 | 1 | δ-OH | tert-Butyl | Cyclopropyl |
| 54 | 1 | δ-OH | tert-Butyl | Cyclopentyl |
| 55 | 1 | α-OCH$_3$ | tert-Butyl | CF$_3$ |
| 56 | 1 | α-OCH$_3$ | tert-Butyl | CHF$_2$ |
| 57 | 1 | α-OCH$_3$ | tert-Butyl | n-Propyl |
| 58 | 1 | α-OCH$_3$ | tert-Butyl | tert-Butyl |
| 59 | 1 | α-OCH$_3$ | tert-Butyl | Cyclopropyl |
| 60 | 1 | α-OCH$_3$ | tert-Butyl | Cyclopentyl |
| 61 | 1 | β-OCH$_3$ | tert-Butyl | CF$_3$ |
| 62 | 1 | β-OCH$_3$ | tert-Butyl | CHF$_2$ |
| 63 | 1 | β-OCH$_3$ | tert-Butyl | n-Propyl |
| 64 | 1 | β-OCH$_3$ | tert-Butyl | tert-Butyl |
| 65 | 1 | β-OCH$_3$ | tert-Butyl | Cyclopropyl |
| 66 | 1 | β-OCH$_3$ | tert-Butyl | Cyclopentyl |
| 67 | 1 | γ-OCH$_3$ | tert-Butyl | CF$_3$ |
| 68 | 1 | γ-OCH$_3$ | tert-Butyl | CHF$_2$ |
| 69 | 1 | γ-OCH$_3$ | tert-Butyl | n-Propyl |
| 70 | 1 | γ-OCH$_3$ | tert-Butyl | tert-Butyl |
| 71 | 1 | γ-OCH$_3$ | tert-Butyl | Cyclopropyl |
| 72 | 1 | γ-OCH$_3$ | tert-Butyl | Cyclopentyl |
| 73 | 1 | δ-OCH$_3$ | tert-Butyl | CF$_3$ |
| 74 | 1 | δ-OCH$_3$ | tert-Butyl | CHF$_2$ |
| 75 | 1 | δ-OCH$_3$ | tert-Butyl | n-Propyl |
| 76 | 1 | δ-OCH$_3$ | tert-Butyl | tert-Butyl |
| 77 | 1 | δ-OCH$_3$ | tert-Butyl | Cyclopropyl |
| 78 | 1 | δ-OCH$_3$ | tert-Butyl | Cyclopentyl |
| 79 | 1 | α-CH$_3$ | tert-Butyl | CF$_3$ |
| 80 | 1 | α-CH$_3$ | tert-Butyl | CHF$_2$ |
| 81 | 1 | α-CH$_3$ | tert-Butyl | n-Propyl |
| 82 | 1 | α-CH$_3$ | tert-Butyl | tert-Butyl |
| 83 | 1 | α-CH$_3$ | tert-Butyl | Cyclopropyl |
| 84 | 1 | α-CH$_3$ | tert-Butyl | Cyclopentyl |
| 85 | 1 | β-CH$_3$ | tert-Butyl | CF$_3$ |
| 86 | 1 | β-CH$_3$ | tert-Butyl | CHF$_2$ |
| 87 | 1 | β-CH$_3$ | tert-Butyl | n-Propyl |
| 88 | 1 | β-CH$_3$ | tert-Butyl | tert-Butyl |
| 89 | 1 | β-CH$_3$ | tert-Butyl | Cyclopropyl |
| 90 | 1 | β-CH$_3$ | tert-Butyl | Cyclopentyl |
| 91 | 1 | γ-CH$_3$ | tert-Butyl | CF$_3$ |
| 92 | 1 | γ-CH$_3$ | tert-Butyl | CHF$_2$ |
| 93 | 1 | γ-CH$_3$ | tert-Butyl | n-Propyl |
| 94 | 1 | γ-CH$_3$ | tert-Butyl | tert-Butyl |
| 95 | 1 | γ-CH$_3$ | tert-Butyl | Cyclopropyl |
| 96 | 1 | γ-CH$_3$ | tert-Butyl | Cyclopentyl |
| 97 | 1 | δ-CH$_3$ | tert-Butyl | CF$_3$ |
| 98 | 1 | δ-CH$_3$ | tert-Butyl | CHF$_2$ |

TABLE A-continued

| No. | m | R | $R^a$ | $R^b$ |
|---|---|---|---|---|
| 99 | 1 | δ-CH₃ | tert-Butyl | n-Propyl |
| 100 | 1 | δ-CH₃ | tert-Butyl | tert-Butyl |
| 101 | 1 | δ-CH₃ | tert-Butyl | Cyclopropyl |
| 102 | 1 | δ-CH₃ | tert-Butyl | Cyclopentyl |
| 103 | 1 | β-C(O)CH₃ | tert-Butyl | CF₃ |
| 104 | 1 | β-C(O)CH₃ | tert-Butyl | CHF₂ |
| 105 | 1 | β-C(O)CH₃ | tert-Butyl | n-Propyl |
| 106 | 1 | β-C(O)CH₃ | tert-Butyl | tert-Butyl |
| 107 | 1 | β-C(O)CH₃ | tert-Butyl | Cyclopropyl |
| 108 | 1 | β-C(O)CH₃ | tert-Butyl | Cyclopentyl |
| 109 | 1 | γ-C(O)CH₃ | tert-Butyl | CF₃ |
| 110 | 1 | γ-C(O)CH₃ | tert-Butyl | CHF₂ |
| 111 | 1 | γ-C(O)CH₃ | tert-Butyl | n-Propyl |
| 112 | 1 | γ-C(O)CH₃ | tert-Butyl | tert-Butyl |
| 113 | 1 | γ-C(O)CH₃ | tert-Butyl | Cyclopropyl |
| 114 | 1 | α-OC₂H₅ | tert-Butyl | CF₃ |
| 115 | 1 | α-OC₂H₅ | tert-Butyl | CHF₂ |
| 116 | 1 | α-OC₂H₅ | tert-Butyl | n-Propyl |
| 117 | 1 | α-OC₂H₅ | tert-Butyl | tert-Butyl |
| 118 | 1 | α-OC₂H₅ | tert-Butyl | Cyclopropyl |
| 119 | 1 | α-OC₂H₅ | tert-Butyl | Cyclopentyl |
| 120 | 1 | β-OC₂H₅ | tert-Butyl | CF₃ |
| 121 | 1 | β-OC₂H₅ | tert-Butyl | CHF₂ |
| 122 | 1 | β-OC₂H₅ | tert-Butyl | n-Propyl |
| 123 | 1 | β-OC₂H₅ | tert-Butyl | tert-Butyl |
| 124 | 1 | β-OC₂H₅ | tert-Butyl | Cyclopropyl |
| 125 | 1 | β-OC₂H₅ | tert-Butyl | Cyclopentyl |
| 126 | 1 | γ-OC₂H₅ | tert-Butyl | CF₃ |
| 127 | 1 | γ-OC₂H₅ | tert-Butyl | CHF₂ |
| 128 | 1 | γ-OC₂H₅ | tert-Butyl | n-Propyl |
| 129 | 1 | γ-OC₂H₅ | tert-Butyl | tert-Butyl |
| 130 | 1 | γ-OC₂H₅ | tert-Butyl | Cyclopropyl |
| 131 | 1 | γ-OC₂H₅ | tert-Butyl | Cyclopentyl |
| 132 | 1 | δ-OC₂H₅ | tert-Butyl | CF₃ |
| 133 | 1 | δ-OC₂H₅ | tert-Butyl | CHF₂ |
| 134 | 1 | δ-OC₂H₅ | tert-Butyl | n-Propyl |
| 135 | 1 | δ-OC₂H₅ | tert-Butyl | tert-Butyl |
| 136 | 1 | δ-OC₂H₅ | tert-Butyl | Cyclopropyl |
| 137 | 1 | δ-OC₂H₅ | tert-Butyl | Cyclopentyl |

The designations α, β, γ, and δ in table A indicate the position of the substituent R on the phenyl ring as shown in the following formula.

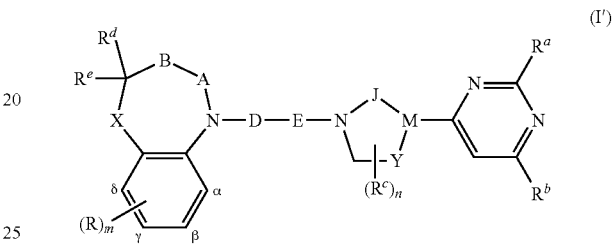

(I')

The compounds I of the invention can be prepared in analogy to the prior art cited at the outset. An important route to the compounds of the invention is depicted in scheme 1.

Scheme 1:

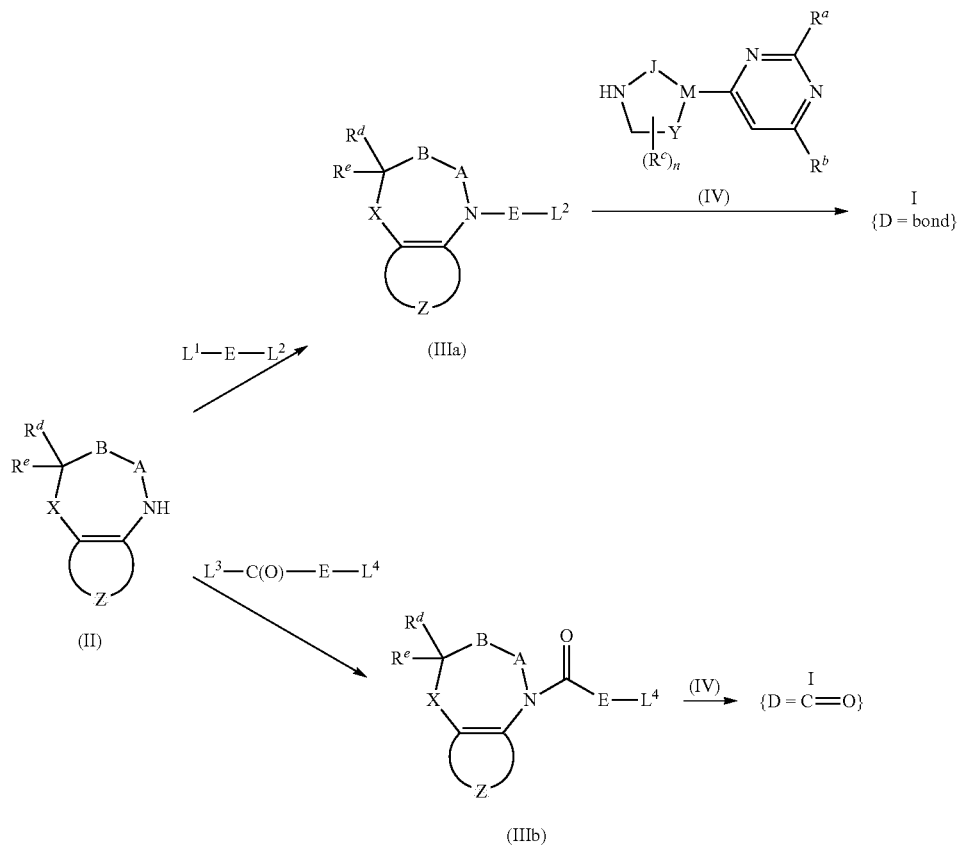

In scheme 1, n, A, B, D, E, X, Z, $R^a$, $R^b$, $R^c$, $R^d$ and $R^e$ have the aforementioned meanings. $L^1$, $L^2$, $L^3$ and $L^4$ are nucleophilically displaceable leaving groups. Examples of suitable nucleophilically displaceable leaving groups $L^1$, $L^2$ and $L^4$ are halogen, in particular chlorine, bromine or iodine, alkyl- and arylsulfonate such as mesylate, tosylate. $L^3$ is for example halogen, in particular chlorine or an active ester residue, e.g. p-nitrophenoxy. $L^1$ and $L^2$ are preferably different from one another and differ in reactivity. For example, $L^1$ is bromine or iodine and $L^2$ is chlorine. The reaction conditions required for the reaction correspond to the reaction conditions usual for nucleophilic substitutions.

Compounds of the general formula IV are either known from the literature, e.g. from WO 96/02519, WO 97/25324, WO 99/02503, WO 00/42036, DE 10304870.7 or the literature cited in these publications, or can be prepared by the processes described therein.

The compounds of the formula II are likewise known and in some cases commercially available or can be prepared in analogy to known processes as described, for example, in: J. Org. Chem. 1981, 46(18), p. 3719, J. Heterocycl. Chem. 2001, 38(4), pp. 961-964, J. Heterocycl. Chem. 1983, 20(3), pp. 663.666, J. Med. Chem. 1986, 29(10), pp. 1832-1840, J. Med. Chem. 2000 43, pp. 3718-3735, J. Med. Chem. 1986, 29(1) pp. 1-8, Chem. Pharm. Bull. 2000, 49(7), pp. 822-829, Org. Lett. 2002, 4(16), pp. 2691-2694, DE 3800386 and EP-A 244697.

The compounds of the invention can in some cases also be prepared by the syntheses depicted in schemes 2a and 2b:

Scheme 2a:

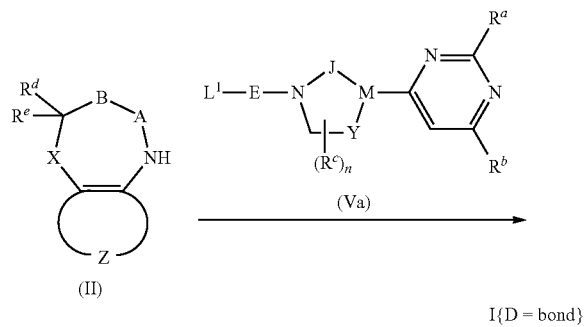

Scheme 2b:

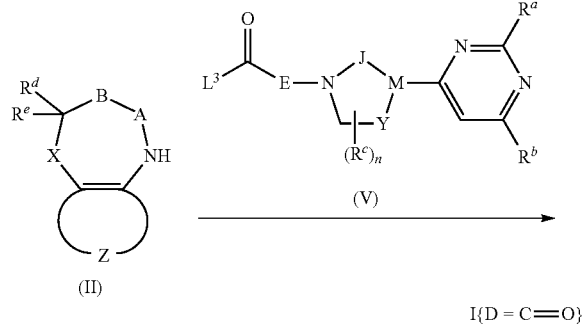

In schemes 2a and 2b, n, A, B, D, E, X, Z, $R^a$, $R^b$, $R^c$, $R^d$ and $R^e$ have the aforementioned meanings. $L^1$ is a nucleophilically displaceable leaving group. $L^1$ is for example chlorine, bromine or iodine. $L^3$ is normally halogen, in particular chlorine or the residue of an active ester group, e.g. 4-nitrophenoxy. The reaction conditions necessary for the reaction correspond to the reaction conditions usual for nucleophilic substitutions on aliphatic compounds, or the reaction takes place under reaction conditions usual for amidation of acid halides.

Compounds of the general formula V are likewise known from the literature, e.g. from WO 96/02519, WO 97/25324, WO 99/02503, WO 00/42036, DE 10304870.7 or from the literature cited in these publications or can be prepared by the processes described therein, for example by reacting a compound of the formula IV shown in scheme 1 with a compound $L^3$-C(O)-E-$L^4$, in which $L^3$, $L^4$ and E have the meanings indicated in scheme 1.

Compounds of the formula I in which A is $CH_2$ can additionally be prepared by reducing compounds I in which A is C=O. Suitable reducing agents comprise for example aluminum hydrides such as lithium aluminum hydride. Suitable methods for this are known from the prior art, e.g. from J. Org. Chem. 1972, 37, p. 2849, and can be employed in an analogous manner for this reaction.

Unless indicated otherwise, the reactions described above generally take place in a solvent at temperatures between room temperature and the boiling point of the solvent used. Alternatively, the energy of activation necessary for the reaction can also be introduced into the reaction mixture using microwaves, which has proved particularly suitable for the reactions catalyzed by transition metals (concerning reactions employing microwaves, see Tetrahedron 2001, 57, pp. 9199 et seq. pp. 9225 et seq., and generally "Microwaves in Organic Synthesis", André Loupy (Ed.), Wiley-VCH 2002).

Examples of solvents which can be used are ethers, such as diethyl ether, diisopropyl ether, methyl tert-butyl ether or tetrahydrofuran, haloalkanes such as dichloromethane, dichloroethane and the like, dimethylformamide, dimethyl sulfoxide, dimethoxyethane, toluene, xylene, acetonitrile, ketones such as acetone or methyl ethyl ketone, or alcohols such as methanol, ethanol or butanol.

If desired, a base is present to neutralize the protons liberated during the reactions. Suitable bases comprise inorganic bases such as sodium carbonate or potassium carbonate, sodium bicarbonate or potassium bicarbonate, also alcoholates such as sodium methoxide, sodium ethoxide, alkali metal hydrides such as sodium hydride, organometallic compounds such as butyllithium or alkylmagnesium compounds, or organic nitrogen bases such as triethylamine or pyridine. The latter may simultaneously serve as solvents.

The crude product is isolated in a conventional way, for example by filtration, removal of the solvent by distillation or extraction from the reaction mixture etc. The resulting compounds can be purified in a conventional way, for example by recrystallization from a solvent, chromatography or conversion into an acid addition salt.

The acid addition salts are prepared in a conventional way by mixing the free base with the appropriate acid, if appropriate in solution in an organic solvent, for example a low molecular weight alcohol such as methanol, ethanol or propanol, an ether such as methyl tert-butyl ether or diisopropyl ether, a ketone such as acetone or methyl ethyl ketone or an ester such as ethyl acetate.

The inventive compounds of the formula I are in general highly selective dopamine $D_3$ receptor ligands which, because of their low affinity for other receptors such as $D_1$ receptors, $D_4$ receptors, α1- and/or α2-adrenergic receptors, muscarinergic receptors, histaminic receptors, opiate receptors and, in particular, for dopamine $D_2$ receptors, have fewer side effects than classical neuroleptics which comprise $D_2$ receptor antagonists.

The high affinity of the inventive compounds for $D_3$ receptors is reflected in very low in vitro $K_i$ values of ordinarily less than 100 nM (nmol/l), frequently less than 50 nM and especially of less than 10 nM or less than 5 nM. Binding affinities for $D_3$ receptors can for example be determined via the displacement of [$^{125}$I]-iodosulpiride in receptor-binding studies.

Particularly important according to the invention are compounds whose selectivity $K_i(D_2)/K_i(D_3)$ is preferably at least 10, even better at least 30 and particularly advantageously at least 50. Receptor-binding studies on $D_1$, $D_2$ and $D_4$ receptors can be carried out for example via the displacement of [$^3$H]SCH23390, [$^{125}$I]iodosulpiride and [$^{125}$I]spiperone.

The compounds can, because of their binding profile, be used for the treatment of conditions which respond to dopamine $D_3$ ligands, i.e. they are effective for the treatment of those disorders or conditions where an influencing (modulation) of dopamine $D_3$ receptors leads to an improvement in the clinical condition or to cure of the disease. Examples of such conditions are disorders or conditions of the central nervous system.

Disorders or conditions of the central nervous system mean disorders affecting the spinal cord or, in particular, the brain. The term "disorder" in the sense according to the invention refers to abnormalities which are usually regarded as pathological states or functions and may reveal themselves in the form of particular signs, symptoms and/or dysfunctions. The inventive treatment may be directed at individual disorders, i.e. abnormalities or pathological states, but it is also possible for a plurality of abnormalities, which are causally connected together if appropriate, to be combined into patterns, i.e. syndromes, which can be treated according to the invention.

The disorders which can be treated according to the invention include in particular psychiatric and neurological disorders. These comprise in particular organic disorders, symptomatic disorders included, such as psychoses of the acute exogenous type or associated psychoses with an organic or exogenous cause, e.g. associated with metabolic disorders, infections and endocrinopathies; endogenous psychoses such as schizophrenia and schizotypal and delusional disorders; affective disorders such as depressions, mania and manic/depressive states; and combined forms of the disorders described above; neurotic and somatoform disorders, and disorders associated with stress; dissociative disorders, e.g. deficits, clouding and splitting of consciousness and personality disorders; disorders of attention and waking/sleeping behavior, such as behavioral disorders and emotional disorders starting in childhood and adolescence, e.g. hyperactivity in children, intellectual deficits, especially attention deficit disorders, disorders of memory and cognition, e.g. learning and memory impairment (impaired cognitive function), dementia, narcolepsy and sleeping disorders, e.g. restless legs syndrome; developmental disorders; anxiety states; delirium; disorders of the sex life, e.g. male impotence; eating disorders, e.g. anorexia or bulimia; addiction; and other undefined psychiatric disorders.

The disorders which can be treated according to the invention also include parkinsonism and epilepsy and, in particular, the affective disorders associated therewith.

Addictive disorders include the psychological disorders and behavioral disorders caused by the abuse of psychotropic substances such as pharmaceuticals or drugs, and other addictive disorders such as, for example, compulsive gambling (impulse control disorders not elsewhere classified). Examples of addictive substances are: opioids (e.g. morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methylamphetamine (Ecstasy); amphetamine and amphetamine-like substances such as methylphenidate or other stimulants, including caffeine. Addictive substances requiring particular attention are opioids, cocaine, amphetamine or amphetamine-like substances, nicotine and alcohol.

With a view to the treatment of addictive disorders, the inventive compounds of the formula I which are particularly preferred are those which themselves have no psychotropic effect. This can also be observed in a test on rats which reduce the self-administration of psychotropic substances, for example cocaine, after administration of compounds which can be used according to the invention.

According to a further aspect of the present invention, the inventive compounds are suitable for the treatment of disorders the causes of which can at least in part be attributed to an abnormal activity of dopamine $D_3$ receptors.

According to another aspect of the present invention, the treatment is directed in particular at those disorders which can be influenced by a binding of, preferably exogenously added, binding partners (ligands) to dopamine $D_3$ receptors in the sense of an expedient medical treatment.

The conditions which can be treated with the inventive compounds are frequently characterized by a progressive development, i.e. the states described above change over the course of time, the severity usually increasing and, if appropriate, states possibly interchanging or other states being added to previously existing states.

The inventive compounds can be used to treat a large number of signs, symptoms and/or dysfunctions associated with the disorders of the central nervous system and in particular the aforementioned states. These include for example a distorted relation to reality, lack of insight and the ability to comply with the usual social norms and demands of life, changes in behavior, changes in individual urges such as hunger, sleep, thirst etc. and in mood, disorders of memory and association, personality changes, especially emotional lability, hallucinations, ego disturbances, incoherence of thought, ambivalence, autism, depersonalization or hallucinations, delusional ideas, staccato speech, absence of associated movement, small-step gait, bent posture of trunk and limbs, tremor, mask-like face, monotonous speech, depression, apathy, deficient spontaneity and irresolution, reduced associationability, anxiety, nervous agitation, stammering, social phobia, panic disorders, withdrawal syndromes associated with dependence, expansive syndromes, states of agitation and confusion, dysphoria, dyskinetic syndromes and tic disorders, e.g. Huntington's chorea, Gilles de la Tourette syndrome, vertigo syndromes, e.g. peripheral postural, rotational and vestibular vertigo, melancholia, hysteria, hypochondria and the like.

A treatment in the sense according to the invention includes not only the treatment of acute or chronic signs, symptoms and/or dysfunctions but also a preventive treatment (prophylaxis), in particular as recurrence or episode prophylaxis. The treatment may be symptomatic, for example directed at suppression of symptom. It may take place short-term, be directed at the medium term or may also be a long-term treatment, for example as part of maintenance therapy.

The inventive compounds are preferably suitable for the treatment of disorders of the central nervous system, especially for the treatment of affective disorders; neurotic disorders, stress disorders and somatoform disorders and psychoses and specifically for the treatment of schizophrenia and depression. Owing to their high selectivity in relation to the $D_3$ receptor, the inventive compounds I are also for the treatment of renal function disorders, especially of renal function disorders caused by diabetes mellitus (see WO 00/67847).

The inventive use of the described compounds comprises a method within the scope of the treatment. This entails the individual to be treated, preferably a mammal, in particular a human or agricultural or domestic animal, being given an effective amount of one or more compounds, usually formulated in accordance with pharmaceutical and veterinary practice. Whether such a treatment is indicated, and the form it is to take, depends on the individual case and is subject to a medical assessment (diagnosis) which takes account of the signs, symptoms and/or dysfunctions present, the risks of developing certain signs, symptoms and/or dysfunctions, and other factors.

The treatment usually takes place by administration once or more than once a day, if appropriate together or alternately with other active ingredients or active ingredient-containing products, so that an individual to be treated is given a daily dose preferably of about 0.1 to 1000 mg/kg of body weight on oral administration or of about 0.1 to 100 mg/kg of body weight on parenteral administration.

The invention also relates to the production of pharmaceutical compositions for the treatment of an individual, preferably a mammal, in particular a human or agricultural or domestic animal. Thus, the ligands are usually administered in the form of pharmaceutical compositions which comprise a pharmaceutically acceptable excipient with at least one ligand of the invention and, if appropriate, further active ingredients. These compositions can be administered for example by the oral, rectal, transdermal, subcutaneous, intravenous, intramuscular or intranasal route.

Examples of suitable pharmaceutical formulations are solid pharmaceutical forms such as oral powders, dusting powders, granules, tablets, especially film-coated tablets, pastilles, sachets, cachets, sugar-coated tablets, capsules such as hard and soft gelatin capsules, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops. Implanted delivery devices can also be used to administer compounds of the invention. A further possibility is also to use liposomes or microspheres.

The compositions are produced by mixing or diluting compounds of the invention usually with an excipient. Excipients may be solid, semisolid or liquid materials which serve as vehicle, carrier or medium for the active ingredient.

Suitable excipients are listed in the relevant pharmaceutical monographs. The formulations may additionally comprise pharmaceutically acceptable carriers or conventional excipients such as lubricants; wetting agents; emulsifying and suspending agents; preservatives; antioxidants; antiirritants; chelating agents; tablet-coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients, such as binders, fillers, lubricants, disintegrants or coatings; propellants; desiccants; opacifiers; thickeners; waxes; plasticizers; white oils.

An arrangement concerning this is based on expert knowledge as set forth for example in Fiedler, H. P., Lexikon der Hilfsstoffe für Pharmazie, Kosmetik and angrenzende Gebiete, 4th edition, Aulendorf: ECV-Editio-Kantor-Verlag, 1996.

The following examples serve to illustrate the invention without limiting it.

The nuclear magnetic resonance spectral properties (NMR) relate to chemical shifts ($\delta$) expressed in parts per million (ppm). The relative area for the shifts in the $^1$H NMR spectrum corresponds to the number of hydrogen atoms for a particular functional type in the molecule. The nature of the shift in terms of multiplicity is indicated as singlet (s), broad singlet (s. br.), doublet (d), broad doublet (d br.), triplet (t), broad triplet (t br.), quartet (q), quintet (quint.), multiplet (m).

A) PREPARATION EXAMPLES

Example 1

1-[2-tert-Butyl-6-(trifluoromethyl)pyrimidin-4-yl]-4-[3-(2-oxo-3,4-dihydroquinolin-1(2H)-yl)propyl]piperazin-4-ium chloride 3,4-Dihydroquinolin-2(1H)-one (3.40 mmol, 0.50 g) in N,N-dimethylformamide (5 ml) was added dropwise to a suspension of NaH (3.74 mmol, 0.15 g, 60%, deoiled) in N,N-dimethylformamide (10 ml) at 10° C., followed by preactivation at room temperature for 1 hour. Then 2-tert-butyl-4-[4-(3-chloropropyl)piperazin-1-yl]-6-(trifluoromethyl)-pyrimidine (3.57 mmol, 1.30 g; prepared as in DE 19728996) in N,N-dimethylformamide (5 ml) was added dropwise. The reaction mixture was stirred at room temperature for 12 hours. After the reaction mixture had been concentrated to dryness, the remaining oil was taken up in 1:1 ethyl acetate/water mixture. The aqueous mixture was extracted with saturated brine. The organic phase was dried over $Na_2SO_4$, the desiccant was filtered off, and the organic phase was concentrated under reduced pressure. The residue obtained in this way was purified by chromatography on silica gel (eluent: heptane:diethyl ether 0-100%), resulting in 840 mg of the title compound.

ESI-MS: [M+Na$^+$]=498.2, [M+H$^+$]=477.2, 476.2, 238.6;

$^1$H-NMR (360 MHz, CDCl$_3$) $\delta$ (ppm): 13.41 (1H, s br.), 7.17 (1H, d), 7.12-6.97 (2H, m) 6.62 (1H, s), 4.53 (1H, s br.), 4.05 (2H, s br.), 3.95 (2H, s br.), 3.65 (2H, s br.), 3.13 (2H, s br.), 2.90 (2H, t), 2.81 (2H, m), 2.65 (2H, t), 2.40 (2H, s br.), 1.30 (9H, s).

Example 2

4-(3-{4-[2-tert-Butyl-6-(trifluoromethyl)pyrimidin-4-yl]piperazin-1-yl}propyl)-2H-1,4-benzoxazin-3(4H)-one 0.24 g of the title compound was obtained starting from 2H-1,4-benzoxazin-3(4H)-one (3.35 mmol, 0.50 g) by the method described in example 1.

ESI-MS: [M+Na$^+$]=500.1, 479.1, [M+H$^+$]=478.1, 239.6.

$^1$H-NMR (500 MHz, CDCl$_3$) $\delta$ (ppm): 7.09-6.97 (4H, m), 6.57 (1H, s), 4.60 (2H, s), 4.07 (2H, t), 3.69 (4H, s br.), 2.53-2.43 (4+2H, m), 1.88 (2H, quint.), 1.33 (9H, s).

Example 3

1-(4-{4-[2-tert-Butyl-6-(trifluoromethyl)pyrimidin-4-yl]piperazin-1-yl}butyl)-3,4-dihydroquinolin-2(1H)-one

3.1 Mixture of 1-(4-chlorobutyl)-3,4-dihydroquinolin-2(1H)-one and 1-(4-bromobutyl)-3,4-dihydroquinolin-2(1H)-one 1.55 g of the mixture of 1-(4-chlorobutyl)-3,4-dihydroquinolin-2(1H)-one and 1-(4-bromobutyl)-3,4-dihydroquinolin-2(1H)-one, which was contaminated with 10% precursor, were obtained starting from 3,4-dihydroquinolin-2(1H)-one (6.79 mmol, 1.00 g) and 1-bromo-4-chlorobutane (8.15 mmol, 1.40 g) by the method described in example 1.

3.2 1-(4-{4-[2-tert-Butyl-6-(trifluoromethyl)pyrimidin-4-yl]piperazin-1-yl}butyl)-3,4-dihydroquinolin-2(1H)-one A mixture of 1-(4-chlorobutyl)-3,4-dihydroquinolin-2(1H)-one and 1-(4-bromobutyl)-3,4-dihydroquinolin-2(1H)-one (0.30 g), 2-tert-butyl-4-piperazin-1-yl-6-(trifluoromethyl)-pyrimidine (1.08 mmol, 0.31 g; prepared as in DE 19735410) and NEt3 (4.54 mmol, 0.46 g) in N,N-dimethylformamide (10 ml) was heated at 100° C. while stirring for 20 hours. The reaction mixture was allowed to cool, ethyl acetate was added, and the reaction mixture was washed twice with water. The combined organic phases were dried over $Na_2SO_4$, the desiccant was filtered off, and the organic phase was concentrated in vacuo. The resulting oily residue was purified by chromatography on silica gel (eluent: methyl tert-butyl ether:methanol 0-100%), resulting in 0.17 g of the title compound.

ESI-MS: [M+Na$^+$]=512.5, 491.5, [M+H$^+$]=490.5;
$^1$H-NMR (500 MHz, CDCl$_3$) δ (ppm): 7.22 (1H, t+CHCl$_3$), 7.15 (1H, d), 7.05 (1H, d), 6.95 (1H, t), 6.58 (1H, s), 3.96 (2H, t), 3.70 (4H, s br.), 2.89 (2H, m), 2.65 (2H, m), 2.51 (4H, quint.), 2.44 (2H, t), 1.71 (2H, quint), 1.61 (2H, quint.), 1.32 (9H, s).

Example 4

1-[2-tert-Butyl-6-(trifluoromethyl)pyrimidin-4-yl]-4-[4-(3-oxo-2,3-dihydro-4H-1,4-benzoxazin-4-yl)butyl]piperazin-4-ium chloride

4.1 Mixture of 4-(4-chlorobutyl)-2H-1,4-benzoxazin-3(4H)-one and 4-(4-bromobutyl)-2H-1,4-benzoxazin-3(4H)-one 7.50 g of the mixture of 4-(4-chlorobutyl)-2H-1,4-benzoxazin-3(4H)-one and 4-(4-bromobutyl)-2H-1,4-benzoxazin-3(4H)-one were obtained starting from 2H-1,4-benzoxazin-3(4H)-one (33.52 mmol, 5.00 g) and 1-bromo-4-chlorobutane (40.23 mmol, 6.90 g) by the method described in example 1.

4.2 1-[2-tert-Butyl-6-(trifluoromethyl)pyrimidin-4-yl]-4-[4-(3-oxo-2,3-dihydro-4H-1,4-benzoxazin-4-yl)butyl]piperazin-4-ium chloride 0.96 g of the title compound was obtained starting from the mixture of 4-(4-chlorobutyl)-2H-1,4-benzoxazin-3(4H)-one and 4-(4-bromobutyl)-2H-1,4-benzoxazin-3(4H)-one (0.50 g) by the method described in example 3.2.
ESI-MS: 493.2, [M+H$^+$]=492.3, 246.6;
$^1$H-NMR (500 MHz, CDCl$_3$) δ (ppm): 7.05-6.96 (2+2H, m), 6.58 (1H, s), 4.59 (2H, s), 3.97 (2H, t), 3.71 (4H, s br.), 2.52 (4H, s br.), 2.45 (2H, m br.), 1.74 (2H, quint.), 1.64 (2H, quint.), 1.34 (9H, s).

Example 5

4-(4-{4-[2-tert-Butyl-6-(trifluoromethyl)pyrimidin-4-yl]piperazin-1-yl}butyl)-6-methyl-2H-1,4-benzoxazin-3(4H)-one

5.1 Mixture of 4-(4-chlorobutyl)-6-methyl-2H-1,4-benzoxazin-3(4H)-one and 4-(4-bromobutyl)-6-methyl-2H-1,4-benzoxazin-3(4H)-one 4.72 g of the mixture of 4-(4-chlorobutyl)-6-methyl-2H-1,4-benzoxazin-3(4H)-one and 4-(4-bromobutyl)-6-methyl-2H-1,4-benzoxazin-3(4H)-one were obtained starting from 6-methyl-2H-1,4-benzoxazin-3(4H)-one (15.69 mmol, 3.00 g; prepared as in J. Heterocycl. Chem. 2001, 38(4), 961-4) and 1-bromo-4-chlorobutane (18.83 mmol, 3.23 g).
ESI-MS: (Cl compound): [M+Na$^+$]=276.0, 256.0, [M+H$^+$]=254.16;
ESI-MS (Br compound): [M+K$^+$]=336.0, [M+H$^+$]=299.0, 298.0.

5.2 4-(4-{4-[2-tert-Butyl-6-(trifluoromethyl)pyrimidin-4-yl]piperazin-1-yl}butyl)-6-methyl-2H-1,4-benzoxazin-3(4H)-one 0.52 g of the title compound was obtained starting from the mixture of 4-(4-chlorobutyl)-6-methyl-2H-1,4-benzoxazin-3(4H)-one and 4-(4-bromobutyl)-6-methyl-2H-1,4-benzoxazin-3(4H)-one (0.50 g) by the method described in example 3.2.
ESI-MS: 507.2, [M+H$^+$]=506.2, 253.6;
$^1$H-NMR (500 MHz, CDCl$_3$) δ (ppm): 6.90-6.85 (1H, m), 6.80-6.75 (2H, m), 6.57 (1H, s), 4.54 (2H, s), 3.95 (2H, t), 3.69 (4H, s br.), 2.49 (4H, m sym.), 2.43 (2H, t), 2.34 (3H, s), 1.73 (2H, quint.), 1.65-1.58 (2H, m), 1.35 (9H, s).

Example 6

4-(4-{4-[2-tert-Butyl-6-(trifluoromethyl)pyrimidin-4-yl]piperazin-1-yl}butyl)-2H-1,4-benzothiazin-3(4H)-one

6.1 Mixture of 4-(4-chlorobutyl)-2H-1,4-benzothiazin-3(4H)-one and 4-(4-bromobutyl)-2H-1,4-benzothiazin-3(4H)-one 3.90 g of the mixture of 4-(4-chlorobutyl)-2H-1,4-benzothiazin-3(4H)-one and 4-(4-bromobutyl)-2H-1,4-benzothiazin-3(4H)-one were obtained starting from 2H-1,4-benzothiazin-3(4H)-one (17.61 mmol, 3.00 g) and 1-bromo-4-chlorobutane (21.14 mmol, 3.62 g) by the method described in example 1.
ESI-MS: (Cl compound): [M+Na$^+$]=278.0, 258.0, 257.0, [M+H$^+$]=256.0;
ESI-MS: (Br compound): [M+K$^+$]=340.0, [M+Na$^+$]=324.0, 302.0, [M+H$^+$]=301.0.

6.2 4-(4-{4-[2-tert-Butyl-6-(trifluoromethyl)pyrimidin-4-yl]piperazin-1-yl}butyl)-2H-1,4-benzothiazin-3(4H)-one 0.31 g of the title compound was obtained starting from the mixture of 4-(4-chlorobutyl)-2H-1,4-benzothiazin-3(4H)- one and 4-(4-bromobutyl)-2H-1,4-benzothiazin-3(4H)-one (0.70 g) by the method described in example 3.2.

ESI-MS: 509.2, [M+H$^+$]=508.3, 254.6;

$^1$H-NMR (500 MHz, CDCl$_3$) δ (ppm): 7.35 (1H, d), 7.22 (1H+CHCl$_3$, t), 7.16 (1H, m), 7.00 (1H, t), 6.56 (1H, s), 4.05 (2H, t), 3.68 (4H, s br.), 3.38 (2H, s), 2.46 (4H, m, sym.), 2.39 (2H, t), 1.75 (2H, quint.), 1.65-1.52 (2H+H$_2$O, m), 1.33 (9H, s).

Example 7

4-(4-{4-[2-tert-Butyl-6-(trifluoromethyl)pyrimidin-4-yl]piperazin-1-yl}butyl)-2-methyl-2H-1,4-benzoxazin-3(4H)-one

7.1 Mixture of 4-(4-chlorobutyl)-2-methyl-2H-1,4-benzoxazin-3(4H)-one and 4-(4-bromobutyl)-2-methyl-2H-1,4-benzoxazin-3(4H)-one 1.90 g of the mixture of 4-(4-chlorobutyl)-2-methyl-2H-1,4-benzoxazin-3(4H)-one and 4-(4-bromobutyl)-2-methyl-2H-1,4-benzoxazin-3(4H)-one were obtained starting from 2-methyl-2H-1,4-benzoxazin-3(4H)-one (18.38 mmol, 3.00 g) and 1-bromo-4-chlorobutane (22.06 mmol, 3.78 g) by the method described in example 1.

ESI-MS: (Cl compound): 256.1, 255.1, [M+H$^+$]=254.1;
ESI-MS: (Br compound): [M+K$^+$]=338.1, [M+Na$^+$]=322.1, 300.1, [M+H$^+$]=299.3, 254.1, 119.2.

7.2 4-(4-{4-[2-tert-Butyl-6-(trifluoromethyl)pyrimidin-4-yl]piperazin-1-yl}butyl)-2-methyl-2H-1,4-benzoxazin-3(4H)-one 1.00 g of the title compound was obtained starting from the mixture of 4-(4-chlorobutyl)-2-methyl-2H-1,4-benzoxazin-3(4H)-one and 4-(4-bromobutyl)-2-methyl-2H-1,4-benzoxazin-3(4H)-one (1.20 g) by the method described in example 3.2.

ESI-MS: 507.2, [M+H$^+$]=506.2, 253.6;

$^1$H-NMR (500 MHz, CDCl$_3$) δ (ppm): 7.03-6.96 (2+2H, m), 6.56 (1H, s), 4.59 (1H, quart.), 3.96 (2H, t), 3.68 (4H, s br.), 2.48 (4H, m), 2.42 (2H, t), 1.73 (2H, m), 1.61 (2H, m), 1.56 (3H, d), 1.33 (9H, s).

Example 8

6-Acetyl-4-(4-{4-[2-tert-butyl-6-(trifluoromethyl)pyrimidin-4-yl]piperazin-1-yl}butyl)-2H-1,4-benzoxazin-3(4H)-one

8.1 Mixture of 6-acetyl-4-(4-chlorobutyl)-2H-1,4-benzoxazin-3(4H)-one and 6-acetyl-4-(4-bromobutyl)-2H-1,4-benzoxazin-3(4H)-one 3.40 g of the mixture of 6-acetyl-4-(4-chlorobutyl)-2H-1,4-benzoxazin-3(4H)-one and 6-acetyl-4-(4-bromobutyl)-2H-1,4-benzoxazin-3(4H)-one were obtained starting from 6-acetyl-2H-1,4-benzoxazin-3(4H)-one (15.69 mmol, 3.00 g) and 1-bromo-4-chlorobutane (18.83 mmol, 3.23 g) by the method described in example 1.

8.2 6-Acetyl-4-(4-{4-[2-tert-butyl-6-(trifluoromethyl)pyrimidin-4-yl]piperazin-1-yl}butyl)-2H-1,4-benzoxazin-3(4H)-one 0.52 g of the title compound was obtained starting from the mixture of 6-acetyl-4-(4-chlorobutyl)-2H-1,4-benzoxazin-3(4H)-one and 6-acetyl-4-(4-bromobutyl)-2H-1,4-benzoxazin-3(4H)-one (1.40 g) by the method described in example 3.2.

ESI-MS: 535.2, [M+H$^+$]=534.2, 267.6;

$^1$H-NMR (500 MHz, CDCl$_3$) δ (ppm): 7.68 (1H, s), 7.60 (1H, d), 7.03 (1H, d), 6.57 (1H, s), 4.66 (2H, s), 4.05 (2H, t), 3.68 (4H, s br.), 2.59 (3H, s), 2.50 (4H, m sym.), 2.43 (2H, t), 1.75 (2H, quint.), 1.63 (2H, m), 1.33 (9H, s).

Example 9

1-(4-{4-[2-Cyclohexyl-6-(trifluoromethyl)pyrimidin-4-yl]piperazin-1-yl}butyl)-3,4-dihydroquinolin-2(1H)-one 0.22 g of the title compound was obtained starting from the mixture of 1-(4-chlorobutyl)-3,4-dihydroquinolin-2(1H)-one and 1-(4-bromobutyl)-3,4-dihydroquinolin-2(1H)-one (0.20 g) from example 3.1 and 2-cyclohexyl-4-piperazin-1-yl-6-(trifluoromethyl)-pyrimidine (0.88 mmol, 0.29 g, prepared as in DE 19735410) by the method described in example 3.2.

ESI-MS: 517.3, [M+H$^+$]=516.3, 258.6.

Example 10

1-((2E)-4-{4-[2-tert-Butyl-6-(trifluoromethyl)pyrimidin-4-yl]piperazin-1-yl}but-2-enyl)-3,4-dihydroquinolin-2(1H)-one 1.35 g of the title compound were obtained starting from 3,4-dihydroquinolinone (3.40 mmol, 0.50 g) and 2-tert-butyl-4-{4-[(2E)-4-chlorobut-2-en-1-yl]piperazin-1-yl}-6-(trifluoromethyl)pyrimidine (3.57 mmol, 1.34 g, prepared as in DE 19728996) by the method described in example 1.

ESI-MS: 489.2, [M+H+]=488.3, 244.6.

Example 11

1-(4-{4-[2-tert-Butyl-6-(trifluoromethyl)pyrimidin-4-yl]piperazin-1-yl}butyl)-4,4-dimethyl-3,4-dihydroquinolin-2(1H)-one

11.1 Mixture of 1-(4-chlorobutyl)-4,4-dimethyl-3,4-dihydroquinolin-2(1H)-one and 1-(4-bromobutyl)-4,4-dimethyl-3,4-dihydroquinolin-2(1H)-one (889-132)

2.50 g of the mixture of 1-(4-chlorobutyl)-4,4-dimethyl-3,4-dihydroquinolin-2(1H)-one and 1-(4-bromobutyl)-4,4-dimethyl-3,4-dihydroquinolin-2(1H)-one were obtained starting from 4,4-dimethyl-3,4-dihydroquinolin-2(1H)-one (11.41 mmol, 2.00 g; prepared as in J. Med. Chem. 1986, 29, 1832-40) and 1-bromo-4-chlorobutane (13.70 mmol, 2.35 g).

ESI-MS: (Cl compound): 269.1, 268.1, 266.1;
ESI-MS: (Br compound): 311.0, 310.0, 266.1.

11.2 1-(4-{4-[2-tert-Butyl-6-(trifluoromethyl)pyrimidin-4-yl]piperazin-1-yl}butyl)-4,4-dimethyl-3,4-dihydroquinolin-2(1H)-one 1.30 g of the title compound were obtained starting from the mixture of 1-(4-chlorobutyl)-4,4-dimethyl-3,4-dihydroquinolin-2(1H)-one and 1-(4-bromobutyl)-4,4-dimethyl-3,4-dihydroquinolin-2(1H)-one (2.00 g).

ESI-MS: 519.3, [M+H$^+$]=518.35, 259.6.

Example 12

1-((2E)-4-{4-[2-tert-Butyl-6-(trifluoromethyl)pyrimidin-4-yl]piperazin-1-yl}-2-methylbut-2-enyl)-3,4-dihydroquinolin-2(1H)-one 0.05 g of the title compound was obtained starting from 3,4-dihydroquinolinone (3.40 mmol, 0.50 g) and 4-(2-tert-butyl-6-trifluoromethyl-pyrimidin-4-yl)-1-(4-chloro-3-methyl-but-2-enyl)piperazin-1-ium chloride (3.57 mmol, 1.52 g, prepared as in DE 19728996) by the method described in example 1.

ESI-MS: 503.3, 502.2, [M+H+]=251.6.

Example 13

6-Acetyl-1-(4-{4-[2-tert-butyl-6-(trifluoromethyl)pyrimidin-4-yl]piperazin-1-yl}butyl)-4,4-dimethyl-3,4-dihydroquinolin-2(1H)-one

13.1 Mixture of 6-acetyl-1-(4-chlorobutyl)-4,4-dimethyl-3,4-dihydroquinolin-2(1H)-one and 6-acetyl-1-(4-bromobutyl)-4,4-dimethyl-3,4-dihydroquinolin-2(1H)-one 1.60 g of the mixture of 6-acetyl-1-(4-chlorobutyl)-4,4-dimethyl-3,4-dihydroquinolin-2(1H)-one and 6-acetyl-1-(4-bromobutyl)-4,4-dimethyl-3,4-dihydroquinolin-2(1H)-one were obtained starting from 6-acetyl-4,4-dimethyl-3,4-dihydroquinolin-2(1H)-one (9.21 mmol, 2.00 g) and 1-bromo-4-chlorobutane (11.05 mmol, 1.89 g) by the method described in example 1.

13.2 6-Acetyl-1-(4-{4-[2-tert-butyl-6-(trifluoromethyl)pyrimidin-4-yl]piperazin-1-yl}butyl)-4,4-dimethyl-3,4-dihydroquinolin-2(1H)-one 0.01 g of the title compound was obtained starting from the mixture of 6-acetyl-1-(4-chlorobutyl)-4,4-dimethyl-3,4-dihydroquinolin-2(1H)-one and 6-acetyl-1-(4-bromobutyl)-4,4-dimethyl-3,4-dihydroquinolin-2(1H)-one (3.25 mmol, 1.00 g) by the method described in example 3.2.

ESI-MS: 561.3, 560.3, [M+H$^+$]=280.6.

Example 14

1-(4-{4-[2-tert-Butyl-6-(trifluoromethyl)pyrimidin-4-yl]piperazin-1-yl}-2-methylbutyl)-3,4-dihydroquinolin-2(1H)-one Pd/C (10%, 10.0 mg) was added to a solution of 1-((2E)-4-{4-[2-tert-butyl-6-(trifluoromethyl)pyrimidin-4-yl]piperazin-1-yl}-2-methylbut-2-enyl)-3,4-dihydroquinolin-2(1H)-one (0.08 mmol, 49.99 mg) from example 12 in methanol (10 ml), and hydrogenation was then carried out at room temperature for 12 hours. 11.10 mg of the title compound were obtained.

ESI-MS: 505.4, 504.4, [M+H$^+$]=252.7.

Example 15

1-(4-{4-[2-tert-Butyl-6-(trifluoromethyl)pyrimidin-4-yl]piperazin-1-yl}pentyl)-3,4-dihydroquinolin-2(1H)-one

15.1 1-(4-Bromopentyl)-3,4-dihydroquinolin-2(1H)-one 1.57 g of the title compound were obtained starting from 3,4-dihydroquinolinone (8.83 mmol, 1.30 g) and 1,4-dibromopentane (9.72 mmol, 2.30 g) by the method described in example 1.

$^1$H-NMR (500 MHz, CDCl$_3$) δ (ppm): 7.26 (1H, t), 7.17 (1H, d), 6.97 (2H, m), 4.17 (1H, m), 3.96 (2H, m), 2.87 (2H, m), 2.64 (2H, m), 1.95-1.74 (4H, m), 1.69 (3H, m).

15.2 1-(4-{4-[2-tert-Butyl-6-(trifluoromethyl)pyrimidin-4-yl]piperazin-1-yl}pentyl)-3,4-dihydroquinolin-2(1H)-one 0.02 g of the title compound was obtained starting from 1-(4-bromopentyl)-3,4-dihydroquinolin-2(1H)-one (1.35 mmol, 0.40 g) by the method described in example 3.2.

ESI-MS: [M+Na$^+$]=526.2, 505.4, [M+H$^+$]=504.4, 252.6;
$^1$H-NMR (500 MHz, CDCl$_3$) δ (ppm): 7.21 (1H, t), 7.16 (1H, d), 7.07 (1H, d), 6.98 (1H, t), 6.55 (1H, s), 4.04-3.96 (1H, m), 3.93-3.84 (1H, m), 3.65 (4H, s br.), 2.88 (2H, m), 2.73-2.58 (1+4H, m), 2.51-2.45 (2H, m), 1.72 (2H, quint.), 1.63-1.54 (1H, m), 1.45-1.37 (1H, m), 1.33 (9H, s), 0.95 (3H, d).

Example 16

1-(5-{4-[2-tert-Butyl-6-(trifluoromethyl)pyrimidin-4-yl]piperazin-1-yl}pentyl)-3,4-dihydroquinolin-2(1H)-one 9.20 mg of the title compound were obtained starting from 3,4-dihydroquinolinone (0.82 mmol, 0.12 g) and 2-tert-butyl-4-[4-(5-chloropentyl)piperazin-1-yl]-6-(trifluoromethyl)pyrimidine (0.77 mmol, 0.30 g; prepared as in DE 19728996) by the method described in example 1.

ESI-MS: 290.0, 274.1, 254.1, 253.1, 252.05.

Example 17

1-(4-{4-[2-tert-Butyl-6-(trifluoromethyl)pyrimidin-4-yl]-1,4-diazepan-1-yl}butyl)-3,4-dihydroquinolin-2(1H)-one 0.17 g of the title compound was obtained starting from the mixture of 1-(4-chlorobutyl)-3,4-dihydroquinolin-2(1H)-one and 1-(4-bromobutyl)-3,4-dihydroquinolin-2(1H)-one (1.39 mmol, 0.33 g) from example 3.1 and 1-(2-tert-butyl-6-trifluoromethyl-pyrimidin-4-yl)-[1,4]diazepane (1.32 mmol, 0.40 g, prepared as in WO 97/25324) by the method described in example 3.2.

ESI-MS: 505.5, [M+H$^+$]=504.45, 252.7.

Example 18

4-[4-(2-tert-Butyl-6-trifluoromethyl-pyrimidin-4-yl)-piperazin-1-yl]-1-(3,4-dihydro-2H-quinolin-1-yl)-butan-1-one

18.1 4-Chloro-1-(3,4-dihydro-2H-quinolin-1-yl)-butan-1-one

5-Chlorobutyral chloride (44.15 mmol, 6.35 g) in dioxane (50 ml) was added dropwise to a suspension of 1,2,3,4-tetrahydroquinoline (30.03 mmol, 4.00 g), potassium carbonate (44.15 mmol, 6.35 g) in dioxane (100 ml) at 10° C. The reaction mixture was stirred at 10° C. for 1 hour and then under reflux for 3 hours. After removal of the salts by filtration, the filtrate was evaporated to dryness. The remaining oil was taken up in dichloromethane and the mixture was extracted three times with 5% strength aqueous NaHCO$_3$ solution (50 ml). It was then neutralized with 0.1 N HCl (20 ml) and washed three times with saturated brine. The organic phase was dried over Na$_2$SO$_4$, the desiccant was filtered off, and the solution was evaporated to dryness, resulting in the title compound.
ESI-MS: 240.1, [M+H$^+$]=238.1, 202.1.

18.2 4-[4-(2-tert-Butyl-6-trifluoromethyl-pyrimidin-4-yl)-piperazin-1-yl]-1-(3,4-dihydro-2H-quinolin-1-yl)-butan-1-one 0.26 g of the title compound was obtained starting from 4-chloro-1-(3,4-dihydro-2H-quinolin-1-yl)-butan-1-one (4.21 mmol, 1.00 g) by the method described in example 3.2.
ESI-MS: [M+H$^+$]=490.2, 245.6.

Example 19

1-(4-{4-[2-tert-Butyl-6-(trifluoromethyl)pyrimidin-4-yl]piperazin-1-yl}butyl)-6-chloro-3,4-dihydro-quinolin-2(1H)-one 19.1 6-Chloro-1-(4-chlorobutyl)-3,4-dihydroquinolin-2(1H)-one 2.90 g of the title compound were obtained starting from 6-chloro-3,4-dihydroquinolin-2(1H)-one (11.01 mmol, 2.00 g; prepared as in J. Med. Chem. 2000, 43, 3718-35) and 1-bromo-4-chlorobutane (13.21 mmol, 2.27 g) by the method described in example 1.

19.2 1-(4-{4-[2-tert-Butyl-6-(trifluoromethyl)pyrimidin-4-yl]piperazin-1-yl}butyl)-6-chloro-3,4-dihydro-quinolin-2(1H)-one 1.34 g of the title compound were obtained starting from 6-chloro-1-(4-chlorobutyl)-3,4-dihydroquinolin-2(1H)-one (4.96 mmol, 1.50 g) by the method described in example 3.2.
ESI-MS: 526.3, [M+H$^+$]=524.3, 263.8, 262.7.
$^1$H-NMR (500 MHz, CDCl$_3$) δ (ppm): 13.28 (1H, s br.), 7.22 (1H, d), 7.16 (1H, s), 6.90 (1H, d), 6.66 (1H, s), 4.54 (2H, s br.), 3.96 (2H, t), 3.63 (2H, s br.), 3.11 (2H, s br.), 2.91 (2H, t), 2.81 (2H, s br.), 2.63 (2H, t), 2.01 (2H, quint. br.), 1.76 (2H, quint.), 1.33 (9H, s).

Example 20

1-(4-{4-[2-tert-Butyl-6-(trifluoromethyl)pyrimidin-4-yl]piperazin-1-yl}butyl)-6-methyl-3,4-dihydro-quinolin-2(1H)-one 20.1 1-(4-Chlorobutyl)-6-methyl-3,4-dihydroquinolin-2(1H)-one 3.90 g of the title compound were obtained starting from 6-methyl-3,4-dihydroquinolin-2(1H)-one (13.65 mmol, 2.20 g; prepared as in J. Med. Chem. 2000, 43, 3718-35) and 1-bromo-4-chlorobutane (16.38 mmol, 2.81 g) by the method described in example 1.

20.2 1-(4-{4-[2-tert-Butyl-6-(trifluoromethyl)pyrimidin-4-yl]piperazin-1-yl}butyl)-6-methyl-3,4-dihydroquinolin-2(1H)-one 0.56 g of the title compound was obtained starting from 1-(4-chlorobutyl)-6-methyl-3,4-dihydroquinolin-2(1H)-one (6.75 mmol, 2.00 g) by the method described in example 3.2.
ESI-MS: 505.5, [M+H$^+$]=504.55, 252.9.

Example 21

1-(4-{4-[2-tert-Butyl-6-(trifluoromethyl)pyrimidin-4-yl]piperazin-1-yl}butyl)-8-methoxy-3,4-dihydro-quinolin-2(1H)-one 21.1 1-(4-Chlorobutyl)-8-methoxy-3,4-dihydro-quinolin-2(1H)-one 1.85 g of the title compound were obtained starting from 8-methoxy-3,4-dihydroquinolin-2(1H)-one (5.42 mmol, 1.20 g; prepared as in Chem. Pharm. Bull. 2001, 49, 822-9) and 1-bromo-4-chlorobutane (6.50 mmol, 1.12 g) by the method described in example 3.2.

21.2 1-(4-{4-[2-tert-Butyl-6-(trifluoromethyl)pyrimidin-4-yl]piperazin-1-yl}butyl)-8-methoxy-3,4-dihydroquinolin-2(1H)-one 1.25 g of the title compound were obtained starting from 1-(4-chlorobutyl)-8-methoxy-3,4-dihydroquinolin-2(1H)-one (5.68 mmol, 1.90 g) by the method described in example 3.2.
ESI-MS: [M+Na$^+$]=542.5, 521.5, [M+H$^+$]=520.5, 260.7.

Example 22

1-(4-{4-[2-tert-Butyl-6-(trifluoromethyl)pyrimidin-4-yl]piperazin-1-yl}butyl)-8-hydroxy-3,4-dihydro-quinolin-2(1H)-one Demethylation of 1-(4-{4-[2-tert-butyl-6-(trifluoromethyl)pyrimidin-4-yl]piperazin-1-yl}butyl)-8-methoxy-3,4-dihydroquinolin-2(1H)-one from example 21 (1.35 mmol, 0.70 g) in dichloromethane (40 ml) with BBr$_3$ (1 M in dichloromethane, 6.74 mmol, 1.67 g) at room temperature over 12 hours afforded 0.41 g of the title compound.
ESI-MS: 507.5, [M+H$^+$]=506.45, 253.8.

Example 23

5-[4-(2-tert-Butyl-6-trifluoromethyl-pyrimidin-4-yl)-piperazin-1-yl]-1-(3,4-dihydro-2H-quinolin-1-yl)-pentan-1-one 23.1 5-Chloro-1-(3,4-dihydro-2H-quinolin-1-yl)-pentan-1-one 7.41 g of the title compound were obtained starting from 1,2,3,4-tetrahydroquinoline (30.03 mmol, 4.00 g) and 5-chlorovaleryl chloride (45.05 mmol, 6.98 g) by the method described in example 18.1.
ESI-MS: [M+H$^+$]=252.1.

23.2 5-[4-(2-tert-Butyl-6-trifluoromethyl-pyrimidin-4-yl)-piperazin-1-yl]-1-(3,4-dihydro-2H-quinolin-1-yl)-pentan-1-one 0.45 g of the title compound was obtained starting from 5-chloro-1-(3,4-dihydro-2H-quinolin-1-yl)-pentan-1-one (7.94 mmol, 2.00 g) by the method described in example 3.2.
ESI-MS: [M+H$^+$]=504.5, 252.9.

Example 24

1-(4-{4-[2-tert-Butyl-6-(trifluoromethyl)pyrimidin-4-yl]piperazin-1-yl}butyl)-8-methyl-3,4-dihydroquinolin-2(1H)-one

24.1 1-(4-Chlorobutyl)-8-methyl-3,4-dihydroquinolin-2(1H)-one 4.00 g of the title compound were obtained starting from 8-methyl-3,4-dihydroquinolin-2(1H)-one (15.51 mmol, 2.50 g; prepared as in J. Med. Chem. 2000, 43, 3718-35) and 1-bromo-4-chlorobutane (18.61 mmol, 3.19 g) by the method described in example 1.

24.2 1-(4-{4-[2-tert-Butyl-6-(trifluoromethyl)pyrimidin-4-yl]piperazin-1-yl}butyl)-8-methyl-3,4-dihydroquinolin-2(1H)-one 1.00 g of the title compound was obtained starting from 1-(4-chlorobutyl)-8-methyl-3,4-dihydroquinolin-2(1H)-one (5.96 mmol, 1.50 g) by the method described in example 3.2.
ESI-MS: [M+Na$^+$]=526.2, 505.4, [M+H$^+$]=504.4, 252.6;
$^1$H-NMR (500 MHz, DMSO-d$_6$) δ (ppm): 11.04 (1H, s br.), 7.18 (1H, s), 7.08 (2H, d), 6.97 (1H, t), 3.86 (2H, t), 3.41 (4H, s), 2.96 (4H, m br.), 2.78 (2H, m sym), 2.40 (2H, m sym.), 2.27 (3H, s), 1.60 (2H, m sym.), 1.38 (2H, quint.), 1.28 (9H, s).

Example 25

1-(4-{4-[2-tert-Butyl-6-(trifluoromethyl)pyrimidin-4-yl]piperazin-1-yl}butyl)-8-chloro-3,4-dihydroquinolin-2(1H)-one

25.1 8-Chloro-1-(4-chlorobutyl)-3,4-dihydroquinolin-2(1H)-one 8.05 g of the title compound were obtained starting from 8-chloro-3,4-dihydroquinolin-2(1H)-one (27.53 mmol, 5.00 g; prepared as in J. Med. Chem. 2000, 43, 3718-35) and 1-bromo-4-chlorobutane (33.04 mmol, 5.66 g) by the method described in example 1.

25.2 1-(4-{4-[2-tert-Butyl-6-(trifluoromethyl)pyrimidin-4-yl]piperazin-1-yl}butyl)-8-chloro-3,4-dihydroquinolin-2(1H)-one 2.45 g of the title compound were obtained starting from 8-chloro-1-(4-chlorobutyl)-3,4-dihydroquinolin-2(1H)-one (7.35 mmol, 2.00 g) by the method described in example 3.2.
ESI-MS: [M+H$^+$]=524.3, 262.6;
$^1$H-NMR (500 MHz, DMSO-d$_6$) δ (ppm): 11.21 (1H, s br.), 7.33 (1H, d), 7.25 (1H, d), 7.18 (1H, s), 7.08 (1H, t), 4.06 (2H, m sym.), 3.46 (4H, s br.), 3.00 (4H, m), 2.88 (2H, m sym.), 2.53-2.47 (2H, m), 1.63 (2H, m sym.), 1.49 (2H, quint.), 1.30 (9H, s).

Example 26

1-(4-{4-[2-tert-Butyl-6-(trifluoromethyl)pyrimidin-4-yl]piperazin-1-yl}butyl)-5-methyl-3,4-dihydroquinolin-2(1H)-one

26.1 1-(4-Chlorobutyl)-5-methyl-3,4-dihydroquinolin-2(1H)-one 1.80 g of the title compound were obtained starting from 5-methyl-3,4-dihydroquinolin-2(1H)-one (6.20 mmol, 1.00 g; prepared as in J. Med. Chem. 2000, 43, 3718-35) and 1-bromo-4-chlorobutane (8.06 mmol, 1.38 g) by the method described in example 1.
ESI-MS: [M+H$^+$]=252.2.

26.2 1-(4-{4-[2-tert-Butyl-6-(trifluoromethyl)pyrimidin-4-yl]piperazin-1-yl}butyl)-5-methyl-3,4-dihydroquinolin-2(1H)-one 0.50 g of the title compound was obtained starting from 1-(4-chlorobutyl)-5-methyl-3,4-dihydroquinolin-2(1H)-one (3.57 mmol, 1.00 g) by the method described in example 3.2.
ESI-MS: [M+H$^+$]=504.4, 252.6.

Example 27

1-(4-{4-[2-tert-Butyl-6-(trifluoromethyl)pyrimidin-4-yl]piperazin-1-yl}butyl)-6-methoxy-3,4-dihydroquinolin-2(1H)-one

27.1 6-Methoxy-3,4-dihydroquinolin-2(1H)-one

6-Hydroxy-3,4-dihydroquinolin-2(1H)-one (18.38 mmol, 3.00 g) was treated in the presence of K$_2$CO$_3$ (22.98 mmol, 3.18 g) with methyl iodide (22.98 mmol, 3.26 g) in N,N-dimethylformamide (30 ml) at room temperature for 24 hours, resulting in 2.05 g of the title compound.
ESI-MS: [M+H+]=178.1.

27.2 Mixture of 1-(4-chlorobutyl)-6-methoxy-3,4-dihydroquinolin-2(1H)-one and 1-(4-bromobutyl)-6-methoxy-3,4-dihydroquinolin-2(1H)-one 3.12 g of the mixture of 1-(4-chlorobutyl)-6-methoxy-3,4-dihydroquinolin-2(1H)-one and 1-(4-bromobutyl)-6-methoxy-3,4-dihydroquinolin-2(1H)-one were obtained starting from 6-methoxy-3,4-dihydroquinolin-2(1H)-one (14.11 mmol, 2.50 g) and 1-bromo-4-chlorobutane (21.16 mmol, 3.63 g) by the method described in example 1.
ESI-MS (bromo compound): 313.0, 312.0;
ESI-MS (chloro compound): 270.1, 260.6.

27.3 1-(4-{4-[2-tert-Butyl-6-(trifluoromethyl)pyrimidin-4-yl]piperazin-1-yl}butyl)-6-methoxy-3,4-dihydroquinolin-2(1H)-one 0.70 g of the title compound was obtained starting from the mixture of 1-(4-chlorobutyl)-6-methoxy-3,4-dihydroquinolin-2(1H)-one and 1-(4-bromobutyl)-6-methoxy-3,4-dihydroquinolin-2(1H)-one (1.00 g) by the method described in example 3.2.
ESI-MS: [M+H$^+$]=520.3, 260.6;
$^1$H-NMR (500 MHz, CDCl$_3$) δ (ppm): 6.94 (1H, d), 6.78-6.70 (2H, m), 6.57 (1H, s), 3.93 (2H, t), 3.80 (3H, s), 3.70 (4H, s br.), 2.85 (2H, t), 2.62 (2H, t), 2.50 (4H, m sym.), 2.42 (2H, t), 1.72-1.63 (2H+H$_2$O, m), 1.59 (2H, quint.), 1.35 (9H, s).

Example 28

1-(4-{4-[2-tert-Butyl-6-(trifluoromethyl)pyrimidin-4-yl]piperazin-1-yl}butyl)-6-hydroxy-3,4-dihydroquinolin-2(1H)-one 0.14 g of the title compound was obtained starting from 1-(4-{4-[2-tert-butyl-6-(trifluoromethyl)pyrimidin-4-yl]piperazin-1-yl}butyl)-6-methoxy-3,4-dihydroquinolin-2(1H)-one from example 27 (0.38 mmol, 0.20 g) by the method described in example 22.

$^1$H-NMR (500 MHz, DMSO-$d_6$) δ (ppm): 7.20 (1H, s), 6.94 (1H, d), 6.66-6.61 (2H, m), 3.85 (2H, m sym.), 3.09 (2H, s br.), 2.76 (2H, t), 2.52 (4H, s br.), 2.43 (2H, t), 1.71 (2H, m br.), 1.53 (2H, quint.), 1.31 (9H, s).

Example 29

1-(4-{4-[2-tert-Butyl-6-(trifluoromethyl)pyrimidin-4-yl]piperazin-1-yl}butyl)-5-methoxy-3,4-dihydro-quinolin-2(1H)-one 29.1 5-Methoxy-3,4-dihydroquinolin-2(1H)-one 1.80 g of the title compound were obtained starting from 5-hydroxy-3,4-dihydroquinolin-2(1H)-one (12.26 mmol, 2.00 g) by the method described in example 27.1.

ESI-MS: [2M+H$^+$]=355.1, [M+H$^+$]=178.1;
$^1$H-NMR (500 MHz, DMSO-$d_6$) δ (ppm): 9.95 (1H, s), 9.60 (1H, s br.), 6.90 (1H, t), 6.47 (1H, d), 6.35 (1H, d), 2.76 (2H, t), 2.38 (2H, t).

29.2 Mixture of 1-(4-chlorobutyl)-5-methoxy-3,4-dihydroquinolin-2(1H)-one and 1-(4-bromobutyl)-5-methoxy-3,4-dihydroquinolin-2(1H)-one 2.80 g of the mixture of 1-(4-chlorobutyl)-5-methoxy-3,4-dihydroquinolin-2(1H)-one and 1-(4-bromobutyl)-5-methoxy-3,4-dihydroquinolin-2(1H)-one were obtained starting from 5-methoxy-3,4-dihydroquinolin-2(1H)-one (9.11 mmol, 1.70 g) and 1-bromo-4-chlorobutane (13.67 mmol, 2.34 g) by the method described in example 1.

ESI-MS: (Br compound): 334.1, 315.1, 312.1;
ESI-MS: (Cl compound): 290.1, 270.2, 268.2.

29.3 1-(4-{4-[2-tert-Butyl-6-(trifluoromethyl)pyrimidin-4-yl]piperazin-1-yl}butyl)-5-methoxy-3,4-dihydroquinolin-2(1H)-one 0.68 g of the title compound was obtained starting from the mixture of 1-(4-chlorobutyl)-5-methoxy-3,4-dihydroquinolin-2(1H)-one and 1-(4-bromobutyl)-5-methoxy-3,4-dihydroquinolin-2(1H)-one (6.03 mmol, 1.70 g) by the method described in example 3.2.

ESI-MS: [M+Na$^+$]=542.5, 521.5, [M+H$^+$]=520.5, 260.9;
$^1$H-NMR (500 MHz, DMSO-$d_6$) δ (ppm): 7.23-7.17 (1H, m), 6.78 (1H, d), 6.74 (1H, d), 3.91 (2H, m sym.), 3.78 (3H, s), 3.06 (4H, s br.), 2.77 (2H, t), 2.51-2.45 (4H, m), 1.71 (2H, m br.), 1.54 (2H, quint.), 1.31 (9H, s).

Example 30

1-(4-{4-[2-tert-Butyl-6-(trifluoromethyl)pyrimidin-4-yl]piperazin-1-yl}butyl)-7-methoxy-3,4-dihydro-quinolin-2(1H)-one 30.1 1-(4-Chlorobutyl)-7-methoxy-3,4-dihydro-quinolin-2(1H)-one 3.93 g of the title compound were obtained starting from 7-methoxy-3,4-dihydroquinolin-2(1H)-one (11.74 mmol, 2.08 g; prepared as in J. Med. Chem. 2000, 43, 3718-35) and 1-bromo-4-chlorobutane (14.09 mmol, 2.42 g) by the method described in example 1.

ESI-MS: [M+K$^+$]=306.1, [M+Na$^+$]=290.0, 270.1, [M+H$^+$]=268.1.

30.2 1-(4-{4-[2-tert-Butyl-6-(trifluoromethyl)pyrimidin-4-yl]piperazin-1-yl}butyl)-7-methoxy-3,4-dihydroquinolin-2(1H)-one 1.54 g of the title compound were obtained starting from 1-(4-chlorobutyl)-7-methoxy-3,4-dihydroquinolin-2(1H)-one (5.87 mmol, 1.97 g) by the method described in example 3.2.

ESI-MS: [M+Na$^+$]=542.5, [M+H$^+$]=521.5, 520.5, 260.7, 119.2;
$^1$H-NMR (400 MHz, CDCl$_3$) δ (ppm): 7.05 (1H, d), 6.66 (1H, s), 6.59 (1H, s), 6.52 (1H, d), 3.92 (2H, t), 3.76 (3H, s), 3.70 (4H, s br.), 2.81 (2H, t), 2.61 (2H, t), 2.50 (4H, t), 2.42 (2H, t), 1.70 (2H, m), 1.58 (2H, quint.), 1.33 (9H, s).

Example 31

1-(4-{4-[2-tert-Butyl-6-(trifluoromethyl)pyrimidin-4-yl]piperazin-1-yl}butyl)-5-hydroxy-3,4-dihydro-quinolin-2(1H)-one 0.09 g of the title compound was obtained starting from 1-(4-{4-[2-tert-butyl-6-(trifluoromethyl)pyrimidin-4-yl]piperazin-1-yl}butyl)-5-methoxy-3,4-dihydroquinolin-2(1H)-one from example 29 (0.38 mmol, 0.20 g) by the method described in example 22.

ESI-MS: [M+Na$^+$]=528.3, 507.2, [M+H$^+$]=506.2, 253.6.

Example 32

1-(4-{4-[2-tert-Butyl-6-(trifluoromethyl)pyrimidin-4-yl]piperazin-1-yl}butyl)-7-hydroxy-3,4-dihydro-quinolin-2(1H)-one 0.39 g of the title compound was obtained starting from 1-(4-{4-[2-tert-butyl-6-(trifluoromethyl)pyrimidin-4-yl]piperazin-1-yl}butyl)-7-methoxy-3,4-dihydroquinolin-2(1H)-one from example 30 (0.94 mmol, 0.49 g) by the method described in example 22.

ESI-MS: [M+H$^+$]=506.2, 253.6;
$^1$H-NMR (400 MHz, CDCl$_3$) δ (ppm): 6.98 (1H, d), 6.62 (1H, s), 6.58 (1H, s), 6.44 (1H, d), 3.90 (2H, t), 3.71 (4H, s br.), 2.78 (2H, t), 2.60 (2H, t), 2.52 (4H, m), 2.43 (2H, t), 1.71 (2H, quint.), 1.60 (2H, quint.), 1.33 (9H, s).

Example 33

1-{4-[4-(2-tert-Butyl-6-propylpyrimidin-4-yl)piperazin-1-yl]butyl}-5-methoxy-3,4-dihydroquinolin-2(1H)-one 0.40 g of the title compound was obtained starting from the mixture of 1-(4-chlorobutyl)-5-methoxy-3,4-dihydroquinolin-2(1H)-one and 1-(4-bromobutyl)-5-methoxy-3,4-dihydroquinolin-2(1H)-one from example 29.2 (0.50 g) and 2-tert-butyl-4-piperazin-1-yl-6-propylpyrimidine (1.77 mmol, 0.47 g; prepared as in DE 19735410) by the method described in example 3.2.

ESI-MS: [M+H$^+$]=494.5, 247.9;
$^1$H-NMR (400 MHz, CDCl$_3$) δ (ppm): 7.17 (1H, t), 6.70 (1H, d), 6.61 (1H, d), 6.11 (1H, s), 3.93 (2H, t), 3.83 (3H, s), 3.61 (4H, s br.), 2.88 (2H, t), 2.57 (2H, t), 2.53 (2H, t), 2.47 (4H, m), 2.39 (2H, t), 1.76-1.53 (9H, m), 1.31 (9H, s), 0.94 (3H, t).

Example 34

1-{4-[4-(2-tert-Butyl-6-propylpyrimidin-4-yl)piper-azin-1-yl]butyl}-5-hydroxy-3,4-dihydroquinolin-2(1H)-one 0.03 g of the title compound was obtained starting from 1-{4-[4-(2-tert-butyl-6-propylpyrimidin-4-yl)piperazin-1-yl]butyl}-5-methoxy-3,4-dihydroquinolin-2(1H)-one from example 33 (0.59 mmol, 0.29 g) by the method described in example 22.

ESI-MS: 481.5, 480.5, 240.9;
$^1$H-NMR (400 MHz, CDCl$_3$) δ (ppm): 7.02 (1H, t), 6.61 (1H, d), 6.50 (1H, d), 6.13 (1H, s), 3.94 (2H, t), 3.64 (4H, s br.), 2.88 (2H, t), 2.58 (2H, t), 2.56-2.47 (4H, m), 2.42 (2H, t), 1.84-1.52 (6H, m), 1.32 (9H, s), 1.26 (2H, t), 0.93 (4H, t).

Example 35

1-(4-{4-[2-tert-Butyl-6-(difluoromethyl)pyrimidin-4-yl]piperazin-1-yl}butyl)-5-methoxy-3,4-dihydro-quinolin-2(1H)-one 0.16 g of the title compound was obtained starting from the mixture of 1-(4-chlorobutyl)-5-methoxy-3,4-dihydroquino-lin-2(1H)-one and 1-(4-bromobutyl)-5-methoxy-3,4-dihyd-roquinolin-2(1H)-one from example 29.2 (0.50 g) and 2-tert-butyl-4-piperazin-1-yl-6-difluoromethylpyrimidine (1.87 mmol, 0.51 g; prepared as in DE 19735410) by the method described in example 3.2.

ESI-MS: [M+H$^+$]=502.2, 251.8;
$^1$H-NMR (400 MHz, CDCl$_3$) δ (ppm): 7.19 (1H, t), 6.71 (1H, d), 6.63 (1H, d), 6.55 (1H, s), 6.36 (1H, s), 3.95 (2H, t), 3.84 (3H, s), 3.68 (4H, s br.), 2.88 (2H, t), 2.58 (2H, t), 2.49 (4H, m), 2.42 (2H, t), 1.69 (2H, quint.), 1.57 (2H, quint.), 1.33 (9H, s).

Example 36

1-(4-{4-[2-tert-Butyl-6-(difluoromethyl)pyrimidin-4-yl]piperazin-1-yl}butyl)-5-hydroxy-3,4-dihydro-quinolin-2(1H)-one 0.03 g of the title compound was obtained starting from 1-(4-{4-[2-tert-butyl-6-(difluoromethyl)pyrimidin-4-yl]pip-erazin-1-yl}butyl)-5-methoxy-3,4-dihydroquinolin-2(1H)-one from example 35 (0.24 mmol, 0.12 g) by the method described in example 22.

ESI-MS: [M+H$^+$]=488.4, 244.8.

Example 37

1-{4-[4-(2-tert-Butyl-6-propylpyrimidin-4-yl)piper-azin-1-yl]butyl}-3,4-dihydroquinolin-2(1H)-one 0.82 g of the title compound was obtained starting from 1-(4-chlorobutyl)-3,4-dihydroquinolin-2(1H)-one and 1-(4-bromobutyl)-3,4-dihydroquinolin-2(1H)-one from example 3.1 (0.59 g) and 2-tert-butyl-4-piperazin-1-yl-6-propylpyri-midine (2.38 mmol, 0.62 g, prepared as in DE 19735410) by the method described in example 3.2.

ESI-MS: [M+H$^+$]=464.4, 232.7;
$^1$H-NMR (400 MHz, CDCl$_3$) δ (ppm): 7.22 (1H, t), 7.16 (1H, d), 7.05 (1H, d), 7.00 (1H, t), 6.13 (1H, s), 3.96 (2H, t), 3.61 (4H, s br.), 2.88 (2H, t), 2.64 (2H, t), 2.59-2.28 (7H, m), 1.76-1.49 (8H, m), 1.33 (9H, s), 0.94 (2H, t).

Example 38

1-{4-[4-(2-tert-Butyl-6-propylpyrimidin-4-yl)piper-azin-1-yl]butyl}-8-methoxy-3,4-dihydroquinolin-2(1H)-one 0.43 g of the title compound was obtained starting from 1-(4-chlorobutyl)-8-methoxy-3,4-dihydroquinolin-2(1H)-one from example 21.1 (3.36 mmol, 1.00 g) and 2-tert-butyl-4-piperazin-1-yl-6-propylpyrimidine (3.36 mmol, 0.88 g; prepared as in DE 19735410) by the method described in example 3.2.

ESI-MS: 495.4, 494.4, [M+H$^+$]=321.2, 247.7;
$^1$H-NMR (400 MHz, CDCl$_3$) δ (ppm): 7.00 (1H, t), 6.80 (1H, d), 6.77 (1H, d), 6.10 (1H, s), 4.07 (2H, t), 3.85 (3H, s), 3.59 (4H, s br.), 2.80 (2H, m), 2.64-2.23 (9H, m incl. 2.32 (2H, t)), 1.69 (2H, sext.), 1.63-1.50 (6H, m), 1.45 (2H, m), 1.31 (9H, s), 0.95 (3H, t).

Example 39

1-{4-[4-(2-tert-Butyl-6-propylpyrimidin-4-yl)piper-azin-1-yl]butyl}-8-hydroxy-3,4-dihydroquinolin-2(1H)-one 42.00 mg of the title compound were obtained starting from 1-{4-[4-(2-tert-butyl-6-propylpyrimidin-4-yl)piper-azin-1-yl]butyl}-8-methoxy-3,4-dihydroquinolin-2(1H)-one from example 38 (0.20 mmol, 0.10 g) by the method described in example 22.

ESI-MS: 480.4, [M+H$^+$]=240.7.

Example 40

1-{4-[4-(2-tert-Butyl-6-propylpyrimidin-4-yl)piper-azin-1-yl]butyl}-5-ethoxy-3,4-dihydroquinolin-2(1H)-one

40.1 5-Ethoxy-3,4-dihydroquinolin-2(1H)-one 2.80 g of the title compound were obtained starting from 5-hydroxy-3,4-dihydroquinolin-2(1H)-one (15.32 mmol, 2.50 g) and ethyl iodide (30.64 mmol, 4.78 g) by the method described in example 27.1.

ESI-MS: [M+H$^+$]=192.1.

40.2 Mixture of 1-(4-chlorobutyl)-5-ethoxy-3,4-di-hydroquinolin-2(1H)-one and 1-(4-bromobutyl)-5-ethoxy-3,4-dihydroquinolin-2(1H)-one 0.67 g of the title compound was obtained starting from 5-ethoxy-3,4-dihydroquinolin-2(1H)-one (2.61 mmol, 0.50 g) and 1-bromo-4-chlorobutane (3.14 mmol, 0.54 g) by the method described in example 1.

ESI-MS: (Br compound): 284.1, 282.1;
ESI-MS: (Cl compound): 282.1, 280.1, 246.1, 102.2.

40.3 1-{4-[4-(2-tert-Butyl-6-propylpyrimidin-4-yl) piperazin-1-yl]butyl}-5-ethoxy-3,4-dihydroquinolin-2(1H)-one 0.16 g of the title compound was obtained starting from the mixture of 1-(4-chlorobutyl)-5-ethoxy-3,4-dihydroquinolin-2(1H)-one and 1-(4-bromobutyl)-5-ethoxy-3,4-dihydro-quinolin-2(1H)-one (0.10 g) and 2-tert-butyl-4-piperazin-1-yl-6-propylpyrimidine (0.35 mmol, 93.13 mg; prepared as in DE19735410) by the method described in example 3.2.

ESI-MS: 508.4, [M+H$^+$]=254.8;

¹H-NMR (400 MHz, CDCl₃) δ (ppm): 7.15 (1H, t), 6.69 (1H, d), 6.60 (1H, d), 6.14 (1H, s), 4.04 (2H, q), 3.94 (2H, t), 3.63 (4H, s br.), 2.88 (2H, t), 2.68-2.26 (10H, m), 1.71 (2H, quint.), 1.59 (4H, s br.), 1.44 (3H, t), 1.32 (9H, s), 0.96 (3H, t).

Example 41

1-{4-[4-(2-tert-Butyl-6-trifluoromethyl-pyrimidin-4-yl)piperazin-1-yl]butyl}-5-ethoxy-3,4-dihydro-1H-quinolin-2-one 46.00 mg of the title compound were obtained starting from the mixture of 1-(4-chlorobutyl)-5-ethoxy-3,4-dihydroquinolin-2(1H)-one and 1-(4-bromobutyl)-5-ethoxy-3,4-dihydroquinolin-2(1/1)-one from example 40.2 (0.05 g) by the method described in example 3.2.

ESI-MS: [M+Na⁺]=556.3, 535.3, [M+H⁺]=534.3, 267.6;
¹H-NMR (400 MHz, DMSO-d₆) δ (ppm): 7.19 (1H, t), 7.03 (1H, s), 6.79 (1H, d), 6.69 (1H, d), 4.03 (2H, quart.), 3.87 (2H, t), 3.68 (3H, s br.), 2.77 (2H, t), 2.63-2.20 (6H, m), 1.53 (4H, m sym.), 1.32 (3H, t), 1.27 (9H, s).

Example 42

1-{4-[4-(2-tert-Butyl-6-trifluoromethyl-pyrimidin-4-yl)piperazin-1-yl]butyl}-3,4,5,6,7,8-hexahydro-1H-quinolin-2-one The title compound was obtained starting from 1-(4-chlorobutyl)-3,4,5,6,7,8-hexahydro-1H-quinolin-2-one (prepared by reacting 3,4,5,6,7,8-hexahydro-1H-quinolin-2-one with 1-bromo-4-chlorobutane by the method in example 1) by the method described in example 3.2.

ESI-MS: [M+Na⁺]=516.3, 495.4, [M+H⁺]=494.4, 247.6;
¹H-NMR (500 MHz, CDCl₃) δ (ppm): 6.56 (1H, s), 3.69 (4H, s br.), 3.57 (2H, m sym.), 2.53-2.37 (8H, m), 2.14 (2H, m sym.), 2.11-2.02 (2H, m), 1.74-1.62 (4H, m), 1.62-1.46 (6H, m), 1.34 (9H, s).

Example 43

1-{4-[4-(2-tert-Butyl-6-trifluoromethyl-pyrimidin-4-yl)piperazin-1-yl]butyl}-1H-quinolin-2-one 43.1 Mixture of 1-(4-chlorobutyl)-1H-quinolin-2-one and 1-(4-bromobutyl)-1H-quinolin-2-one The mixture of 1-(4-chlorobutyl)-1H-quinolin-2-one and 1-(4-bromobutyl)-1H-quinolin-2-one was obtained by the method described in example 3.1.

ESI-MS (Cl compound): 238.1, 236.1;
ESI-MS (Br compound): [M+Na⁺]=302.0, [M+H⁺]=280.0, 236.1.

43.2 1-{4-[4-(2-tert-Butyl-6-trifluoromethyl-pyrimidin-4-yl)piperazin-1-yl]butyl}-1H-quinolin-2-one The title compound was obtained starting from the mixture of 1-(4-chlorobutyl)-1H-quinolin-2-one and 1-(4-bromobutyl)-1H-quinolin-2-one by the method described in example 3.2.

ESI-MS: [M+Na⁺]=510.2, 489.2, [M+H⁺]=488.3, 244.6;
¹H-NMR (500 MHz, CDCl₃) δ (ppm): 7.66 (1H, d), 7.58-7.51 (2H, m), 7.43 (1H, d), 7.20 (1H, t), 6.69 (1H, d), 6.56 (1H, s), 4.33 (2H, t), 3.68 (4H, s br.), 2.51 (4H, m sym.), 2.45 (2H, t), 1.82 (2H, quint.), 1.68 (2H, quint.), 1.34 (9H, s).

Example 44

1-{4-[4-(2-tert-Butyl-6-propyl-pyrimidin-4-yl)piperazin-1-yl]butyl}-4,6,7,8-tetrahydro-1H,3H-quinoline-2,5-dione 44.1 Mixture of 1-(4-chlorobutyl)-4,6,7,8-tetrahydro-1H,3H-quinoline-2,5-dione and 1-(4-bromobutyl)-4,6,7,8-tetrahydro-1H,3H-quinoline-2,5-dione The mixture of 1-(4-chlorobutyl)-4,6,7,8-tetrahydro-1H,3H-quinoline-2,5-dione and 1-(4-bromobutyl)-4,6,7,8-tetrahydro-1H,3H-quinoline-2,5-dione was obtained by the method described in example 3.1.

ESI-MS (Cl compound): 258.1, 256.1;
ESI-MS (Br compound): 301.0, 300.0.

44.2 1-{4-[4-(2-tert-Butyl-6-propyl-pyrimidin-4-yl)piperazin-1-yl]butyl}-4,6,7,8-tetrahydro-1H,3H-quinoline-2,5-dione The title compound was obtained starting from the 1-(4-chlorobutyl)-4,6,7,8-tetrahydro-1H,3H-quinoline-2,5-dione and 1-(4-bromobutyl)-4,6,7,8-tetrahydro-1H,3H-quinoline-2,5-dione mixture by the method described in example 3.2.

ESI-MS: [M+H⁺]=482.4, 241.7;
¹H-NMR (400 MHz, CDCl₃) δ (ppm): 6.12 (1H, s), 3.72 (2H, t), 3.62 (4H, s br.), 2.81-2.28 (16H, m; incl. 2.41 (4H, s)), 2.09 (2H, quint.), 1.70 (2H, sext.), 1.60 (4H+H₂O, s br.), 1.31 (9H, s), 0.95 (3H, t).

Example 45

1-{4-[4-(2-tert-Butyl-6-trifluoromethyl-pyrimidin-4-yl)piperazin-1-yl]butyl}-4,6,7,8-tetrahydro-1H,3H-quinoline-2,5-dione Preparation took place by a process based on that described in example 44.

ESI-MS: [M+K⁺]=546.3, [M+H⁺]=508.3;
¹H-NMR (400 MHz, CDCl₃) δ (ppm): 6.57 (1H, s), 3.73 (6H, s br.), 2.70-2.32 (14H, m), 2.09 (2H, quint.), 1.57 (6H, s br.), 1.33 (9H, s).

Example 46

1-{4-[4-(2-tert-Butyl-6-propylpyrimidin-4-yl)piperazin-1-yl]butyl}-1,3,4,5-tetrahydro-2H-1-benzazepin-2-one 46.1 Mixture of 1-(4-chlorobutyl)-1,3,4,5-tetrahydro-2H-1-benzazepin-2-one and 1-(4-bromobutyl)-1,3,4,5-tetrahydro-2H-1-benzazepin-2-one 1.53 g of the mixture of 1-(4-chlorobutyl)-1,3,4,5-tetrahydro-2H-1-benzazepin-2-one and 1-(4-bromobutyl)-1,3,4,5-tetrahydro-2H-1-benzazepin-2-one were obtained as approximately 1:1 mixture starting from 1,3,4,5-tetrahydro-2H-1-benzazepin-2-one (6.20 mmol, 1.00 g; prepared as in J. Heterocycl. Chem. 1983, 20, 663-6) and 1-bromo-4-chlorobutane (7.44 mmol, 1.28 g) by the method described in example 1.
ESI-MS (Cl compound): [M+H+]=252.1;
ESI-MS (Br compound): [M+H+]=296.0.

46.2 1-{4-[4-(2-tert-Butyl-6-propylpyrimidin-4-yl)piperazin-1-yl]butyl}-1,3,4,5-tetrahydro-2H-1-benzazepin-2-one 0.49 g of the title compound was obtained starting from the mixture of 1-(4-chlorobutyl)-1,3,4,5-tetrahydro-2H-1-benzazepin-2-one and 1-(4-bromobutyl)-1,3,4,5-tetrahydro-2H-1-benzazepin-2-one (2.86 mmol, 0.80 g) and 2-tert-butyl-4-piperazin-1-yl-6-propylpyrimidine (2.86 mmol, 0.75 g; prepared as in DE 19735410) by the method described in example 3.2.
ESI-MS: [M+H$^+$]=478.4, 239.7.

Example 47

5-{4-[4-(2-tert-Butyl-6-propylpyrimidin-4-yl)piperazin-1-yl]butyl}-2,3-dihydro-1,5-benzothiazepin-4(5H)-one

47.1 5-(4-Chlorobutyl)-2,3-dihydro-1,5-benzothiazepin-4(5H)-one 4.60 g of the title compound were obtained starting from 2,3-dihydro-1,5-benzothiazepin-4(5H)-one (27.90 mmol, 5.00 g; prepared as in DE 3800386) and 1-bromo-4-chlorobutane (33.47 mmol, 5.74 g) by the method described in example 1.
ESI-MS: [M+H$^+$]=270.0.

47.2 5-{4-[4-(2-tert-Butyl-6-propylpyrimidin-4-yl)piperazin-1-yl]butyl}-2,3-dihydro-1,5-benzothiazepin-4(5H)-one 0.58 g of the title compound was obtained starting from 5-(4-chlorobutyl)-2,3-dihydro-1,5-benzothiazepin-4(5H)-one (2.67 mmol, 0.80 g) and 2-tert-butyl-4-piperazin-1-yl-6-propylpyrimidine (2.67 mmol, 0.70 g; prepared as in DE 19735410) by the method described in example 3.2.
ESI-MS: [M+H+]=496.4, 248.7.

Example 48

1-(5-{4-[2-tert-Butyl-6-(trifluoromethyl)pyrimidin-4-yl]piperazin-1-yl}pentanoyl)-2,3,4,5-tetrahydro-1H-1-benzazepine

48.1 1-(5-Chloropentanoyl)-2,3,4,5-tetrahydro-1H-1-benzazepine 4.25 g of the title compound were obtained starting from 2,3,4,5-tetrahydro-1H-1-benzazepine (16.13 mmol, 2.50 g; prepared as in Org. Lett. 2002, 4, 261-4) and 5-chlorovaleryl chloride (24.20 mmol, 3.75 g) by the method described in example 18.1.
ESI-MS: 269.1, 268.1, 266.1.

48.2 1-(5-{4-[2-tert-Butyl-6-(trifluoromethyl)pyrimidin-4-yl]piperazin-1-yl}pentanoyl)-2,3,4,5-tetrahydro-1H-1-benzazepine 0.67 g of the title compound was obtained starting from 1-(5-chloropentanoyl)-2,3,4,5-tetrahydro-1H-1-benzazepine (1.88 mmol, 0.50 g) by the method described in example 3.2.
ESI-MS: [M+H$^+$]=518.2, 259.8.

Example 49

1-{5-[4-(2-tert-Butyl-6-propylpyrimidin-4-yl)piperazin-1-yl]pentanoyl}-2,3,4,5-tetrahydro-1H-1-benzazepine 0.60 g of the title compound was obtained starting from 1-(5-chloropentanoyl)-2,3,4,5-tetrahydro-1H-1-benzazepine from example 48.1 (1.88 mmol, 0.50 g) and 2-tert-butyl-4-piperazin-1-yl-6-propylpyrimidine (1.88 mmol, 0.49 g; prepared as in DE 19735410) by the method described in example 3.2.
ESI-MS: [M+H$^+$]=492.7, 246.97.

Example 50

1-(4-{4-[2-tert-Butyl-6-(trifluoromethyl)pyrimidin-4-yl]piperazin-1-yl}butyl)-1,3,4,5-tetrahydro-2H-1-benzazepin-2-one A mixture of 1-(4-chlorobutyl)-1,3,4,5-tetrahydro-2H-1-benzazepin-2-one and 1-(4-bromobutyl)-1,3,4,5-tetrahydro-2H-1-benzazepin-2-one (0.40 g), 2-tert-butyl-4-piperazin-1-yl-6-(trifluoromethyl)pyrimidine (1.59 mmol, 0.46 g, prepared as in DE 19735410), NaBr (7.94 mmol, 0.82 g), diisopropylethylamine (15.57 mmol, 2.01 g) and N-methylpyrrolidinone (0.6 ml) was heated at 120° C. for 5 hours. The suspension was then filtered, and the filtrate was evaporated to dryness. The residue was taken up in ethyl acetate and extracted with saturated brine. The organic phase was dried, the desiccant was filtered off, and the solution was evaporated to dryness. The residue was purified by chromatography on silica gel (eluent: dichloromethane/MeOH (0-100%), resulting in 0.58 g of the title compound.
ESI-MS: [M+H$^+$]=504.4, 252.7.

Example 51

5-(4-{4-[2-tert-Butyl-6-(trifluoromethyl)pyrimidin-4-yl]piperazin-1-yl}butyl)-2,3-dihydro-1,5-benzothiazepin-4(5H)-one 0.57 g of the title compound was obtained starting from 5-(4-chlorobutyl)-2,3-dihydro-1,5-benzothiazepin-4(5H)-one from example 47.1 (2.79 mmol, 0.50 g) by the method described in example 50.
ESI-MS: [M+H$^+$]=522.2, 261.6.

Example 52

4-[4-(2-tert-Butyl-6-trifluoromethyl-pyrimidin-4-yl)piperazin-1-yl]-1-(2,3,4,5-tetrahydro-benzo[b]azepin-1-yl)-butan-1-one

52.1 4-Chloro-1-(2,3,4,5-tetrahydro-benzo[b]azepin-1-yl)-butan-1-one 0.80 g of the title compound was obtained starting from 2,3,4,5-tetrahydro-1H-1-benzazepine (3.40 mmol, 0.50 g; prepared as in Org. Lett. 2002, 4, 261-4) and 5-chlorobutyral chloride (5.09 mmol, 0.73 g) by the method described in example 18.1.
ESI-MS: [M+H$^+$]=252.1.

52.2 4-[4-(2-tert-Butyl-6-trifluoromethyl-pyrimidin-4-yl)piperazin-1-yl]-1-(2,3,4,5-tetrahydro-benzo[b]azepin-1-yl)-butan-1-one 0.42 g of the title compound was obtained starting from 4-chloro-1-(2,3,4,5-tetrahydro-benzo[b]azepin-1-yl)-butan-1-one (1.19 mmol, 0.30 g) by the method described in example 3.2.

ESI-MS: [M+H$^+$]=504.4, 252.6.

Example 53

4-[4-(2-tert-Butyl-6-propyl-pyrimidin-4-yl)piperazin-1-yl]-1-(2,3,4,5-tetrahydrobenzo[b]azepin-1-yl)-butan-1-one 0.36 g of the title compound was obtained starting from 4-chloro-1-(2,3,4,5-tetrahydro-benzo[b]azepin-1-yl)-butan-1-one from example 52.1 (1.19 mmol, 0.30 g) and 2-tert-butyl-4-piperazin-1-yl-6-propylpyrimidine (1.19 mmol, 0.31 g; prepared as in DE 19735410) by the method described in example 3.2.

ESI-MS: [M+H$^+$]=478.4.

The compounds of examples 54 to 57 were prepared in an analogous manner:

Example 54

1-{4-[4-(2-tert-Butyl-6-propyl-pyrimidin-4-yl)piperazin-1-yl]butyl}-6-methoxy-1,3,4,5-tetrahydro-benzo[b]azepin-2-one ESI-MS: [M+Na$^+$]=530.5, 509.5, [M+H$^+$]=508.5, 254.9; $^1$H-NMR (400 MHz, DMSO-d$_6$) δ (ppm): 7.28 (1H, t), 6.96 (1H, d), 6.89 (1H, d), 6.41 (1H, s), 3.80 (3H, s), 3.53 (4H, s br.), 2.45 (2H, t), 2.31 (4H, s br.), 2.19 (2H, t), 2.06 (2H, s), 1.63 (2H, sext.), 1.54-1.32 (4H, m), 1.25 (9H, s), 0.89 (3H, t).

Example 55

4-(2-tert-Butyl-6-trifluoromethylpyrimidin-4-yl)-1-[4-(6-methoxy-2-oxo-2,3,4,5-tetrahydro-benzo[b]azepin-1-yl)butyl]piperazine as fumarate

ESI-MS: [M+H$^+$]=534.2, 267.6;

Example 56

4-(2-tert-butyl-6-propyl-pyrimidin-4-yl)-1-[4-(6-hydroxy-2-oxo-2,3,4,5-tetrahydro-benzo[b]azepin-1-yl)butyl]piperazine as fumarate ESI-MS: [M+H$^+$]=494.5, 247.7; $^1$H-NMR (400 MHz, DMSO-d$_6$) δ (ppm): 9.55 (1H, s), 7.09 (1H, t), 6.79 (1H, d), 6.71 (1H, d), 6.43 (1H, s), 3.54 (4H, s br.), 2.46 (2H, t), 2.36 (4H, m), 2.25 (2H, t), 2.08 (2H, s br.), 1.63 (2H, sext.), 1.39 (4H, m), 1.25 (9H, s), 0.90 (3H, t).

Example 57

4-(2-tert-Butyl-6-trifluoromethyl-pyrimidin-4-yl)-1-[4-(6-hydroxy-2-oxo-2,3,4,5-tetrahydro-benzo[b]azepin-1-yl)butyl]piperazine as fumarate ESI-MS: [M+Na$^+$]=542.3, 521.3, [M+H$^+$]=520.2, 260.6.

B) EXAMPLES OF PHARMACEUTICAL ADMINISTRATION FORMS

Tablets:
Tablets of the following composition are compressed in a tablet press in a conventional way:
40 mg of substance of example 2
120 mg of corn starch
13.5 mg of gelatin
45 mg of lactose
2.25 mg of Aerosil® (chemically pure silica in submicroscopically fine distribution)
6.75 mg of potato starch (as 6% strength paste)
Sugar-Coated Tablets:
20 mg of substance of example 2
60 mg of core composition
70 mg of sugar-coating composition The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The sugar-coated tablets produced in this way are subsequently provided with an enteric coating.

C) BIOLOGICAL INVESTIGATIONS

Receptor Binding Studies

The substance to be tested was dissolved either in methanol/Chremophor® (BASF-AG) or in dimethyl sulfoxide and then diluted with water to the desired concentration.

I. Dopamine D$_3$ Receptor:

The mixture (0.250 ml) was composed of membranes from ~10$^6$ HEK-293 cells with stably expressed human dopamine D$_3$ receptors, 0.1 nM [$^{125}$I]-iodosulpiride and incubation buffer (total binding) or with additional test substance (inhibition plot) or 1 μM spiperone (nonspecific binding). Triplicate mixtures were carried out.

The incubation buffer comprised 50 mM Tris, 120 mM NaCl, 5 mM KCl, 2 mM CaCl$_2$, 2 mM MgCl$_2$ and 0.1% bovine serum albumin, 10 μM quinolone, 0.1% ascorbic acid (prepared fresh each day). The buffer was adjusted to pH 7.4 with HCl.

II. Dopamine D$_{2L}$ Receptor:

The mixture (1 ml) was composed of membranes from ~10$^6$ HEK-293 cells with stably expressed human dopamine D$_{2L}$ receptors (long isoform) and 0.01 nM [$^{125}$I]-iodospiperone and incubation buffer (total binding) or with additional test substance (inhibition plot) or 1 μM haloperidol (nonspecific binding). Triplicate mixtures were carried out.

The incubation buffer comprised 50 mM Tris, 120 mM NaCl, 5 mM KCl, 2 mM CaCl$_2$, 2 mM MgCl$_2$ and 0.1% bovine serum albumin. The buffer was adjusted to pH 7.4 with HCl.

III. Measurement and Evaluation:

After incubation at 25° C. for 60 minutes, the mixtures were filtered under vacuum through Whatman GF/B glass fiber filters using a cell harvester. The filters were transferred by a filter transfer system into scintillation vials. After addition of 4 ml of Ultima Gold® (Packard), the samples were shaken for one hour and then the radioactivity was counted in a beta counter (Packard, Tricarb 2000 or 2200CA). The cp values were converted into dpm by means of a standard quench series with the aid of the instrument's own program.

Evaluation of the inhibition plots took place by iterative nonlinear regression analysis using the Statistical Analysis System (SAS) similar to the "LIGAND" program described by Munson and Rodbard.

In these assays, the inventive compounds show very good affinities for the $D_3$ receptor (<100 nM, frequently <50 nM and especially <10 nM) and bind selectively to the $D_3$ receptor.

The results of the binding assays are indicated in table 1.

TABLE 1

| Example | $K_i$ ($D_3$) [nM] | Selectivity vs. $D_2L$* |
|---------|--------------------|-------------------------|
| 1       | 3.43               | 37                      |
| 2       | 12.1               | 29                      |
| 10      | 9.2                | 28                      |
| 33      | 1.71               | 65                      |
| 36      | 1.18               | 41                      |
| 37      | 1.59               | 38                      |
| 44      | 1.54               | 29                      |
| 45      | 4.68               | 41                      |
| 54      | 2.25               | 25                      |
| 56      | 0.69               | 26                      |
| 57      | 2.48               | 38                      |

*$K_i(D_{2L})/K_i(D_3)$

We claim:
1. A compound of the formula I

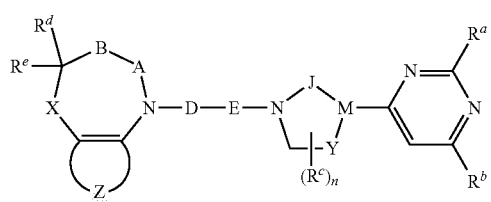

in which
A is a C=W or $CR^f R^g$ group;
B is a chemical bond or a $CR^h R^i$ group;
X is O, S, an N—$R^k$ group or a $CR^m R^n$ group;
D is C=O or a chemical bond;
E is a linear or branched 2 to 10 membered alkylene chain which may have as chain members 1 or 2 non-adjacent heteroatomic group(s) K which is selected from O, S, S(O), S(O)$_2$ and N—$R^p$, and which may comprise a carbonyl group and/or a cycloalkanediyl group and/or may have a double or triple bond;
W is oxygen or sulfur;
Z forms together with the C atoms to which it is bonded a fused 5-, 6- or 7-membered carbocycle or heterocycle which has 1, 2, 3 or 4 heteroatoms which are selected from N, O and S, where the fused carbocycle and the fused heterocycle may have 1 or 2 carbonyl groups as ring members and/or 1, 2, 3 or 4 substituents R which are selected from optionally substituted $C_1$-$C_6$-alkyl, CN, OR$^1$, NR$^2$R$^3$, NO$_2$, SR$^4$, SO$_2$R$^4$, SO$_2$NR$^2$R$^3$, CONR$^2$R$^3$, COOR$^5$, COR$^6$, $C_1$-$C_4$-haloalkoxy, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkyloxy and halogen and/or 2 substituents R may together form a chain X'-Alk'-X" in which X' and X" are independently of one another O or S, and Alk' is $C_1$-$C_4$-alkanediyl which optionally has 1, 2, 3 or 4 alkyl groups or halogen atoms as substituents;

J is $C_2$—$CH_2$;
M is N;
Y is $CH_2$—$CH_2$;
n is 0 or 1;
$R^a$, $R^b$ are independently of one another selected from optionally substituted $C_1$-$C_6$-alkyl, $C_2$-$C_6$-alkenyl, $C_2$-$C_6$-alkynyl, $C_3$-$C_6$-cycloalkyl, $C_4$-$C_{10}$-bicycloalkyl and $C6$-$C_{10}$-tricycloalkyl, where the last three groups mentioned may optionally be substituted by halogen or $C_1$-$C_4$-alkyl, or halogen, CN, OR$^1$, NR$^2$R$^3$, NO$_2$, SR$^4$, SO$_2$R$^5$, CONR$^2$R$^3$, SO$_2$NR$^2$R$^3$, COOR$^5$, COR$^6$, O-COR$^6$, 5- or 6-membered heterocyclyl having 1, 2 or 3 heteroatoms selected from O, S and N, and phenyl, where phenyl and heterocyclyl may optionally have 1, 2 or 3 substituents which are selected independently of one another from $C_1$-$C_4$-alkyl, $C_1$-$C_4$-alkoxy, NR$^2$R$^3$, CN, $C_1$-$C_2$-fluoroalkyl and halogen;
$R^c$ is $C_1$-$C_4$-alkyl;
$R^d$, $R^e$ are independently of one another selected from hydrogen, halogen, optionally substituted $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_3$-$C_6$-cycloalkyloxy, $C_3$-$C_6$-cycloalkyl-$C_1$-$C_4$-alkyloxy and optionally substituted phenyl, where $CR^d R^e$ may together be C=O, and the radicals $R^d$, $R^e$ may together form a chain X'-Alk-X" in which X' and X" are independently of one another O or S, and Alk is $C_2$-$C_4$-alkanediyl which optionally has 1, 2, 3, or 4 alkyl groups or halogen atoms as substituents;
$R^f$, $R^g$ are independently of one another hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl, or the radicals $R^f$, $R^g$ may together form a chain X'-Alk-X" in which Alk, X' and X" have the aforementioned meanings;
$R^h$, $R^i$ are independently of one another hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl;
$R^k$, $R^p$ are independently of one another hydrogen, $C_1$-$C_4$-alkyl, $C_1$-$C_6$-alkoxy, $C_1$-$C_6$-alkoxyalkyl, $C_1$-$C_6$-alkylcarbonyl, $C_1$-$C_6$-alkoxycarbonyl, phenylalkyl, phenylcarbonyl, phenoxycarbonyl, where phenyl in the last three groups mentioned may have 1, 2 or 3 substituents which are selected from $C_1$-$C_4$-alkyl, $C_1$-$C_4$-alkoxy, NR$^2$R$^3$, CN, $C_1$-$C_2$-fluoroalkyl and halogen;
$R^m$, $R^n$ are independently of one another hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl; and
in the case where X is $CR^m R^n$ or N—$R^k$, one of the radicals $R^d$ or $R^e$ may together with one of the radicals $R^m$, $R^n$ or $R^k$ also be a π bond; and
$R^1$, $R^2$, $R^3$, $R^4$, $R^5$ and $R^6$ are independently of one another H, optionally substituted $C_1$-$C_6$-alkyl or optionally substituted phenyl, where $R^3$ may also be a group COR$^7$, where $R^7$ is hydrogen, optionally substituted $C_1$-$C_1$-alkyl or optionally substituted phenyl, where $R^2$ with $R^3$ may also form together with the nitrogen atom to which they are bonded a 5- or 6-membered, saturated or unsaturated heterocycle which may have a further heteroatom selected from O, S and NR$^8$ as ring member, where R$^8$ is hydrogen or $C_1$-$C_4$-alkyl;
or a physiologically acceptable acid addition salt thereof.

2. The compound of the formula I of claim 1, in which Z together with the C atoms to which it is bonded stands for a fused phenyl ring which may have 1, 2, 3 or 4 of the aforementioned substituents R.

3. The compound of the formula I of claim 1, in which either A is a C=W group or D is C=O.

4. The compound of the formula I of claim 1, in which E is a $(CH_2)_k$ group in which k is 3, 4, 5 or 6.

5. The compound of the formula I of claim 1, in which B is a chemical bond.

6. The compound of the formula I of claim 1, in which B is $CH_2$.

7. The compound of the formula I of claim 1, in which $R^a$ and $R^b$ are independently of one another $C_1$-$C_6$-alkyl, $C_1$-$C_6$-haloalkyl, $C_2$-$C_6$-alkenyl, $C_3$-$C_6$-cycloalkyl, $C_1$-$C_6$-alkoxy-$C_1$-$C_4$-alkyl or $C_3$-$C_6$-cycloalkyl-$C_1$-$C_4$-alkyl.

8. The compound of the formula I of claim 7, in which $R^a$ is $C_1$-$C_6$-alkyl, and $R^b$ is selected from $C_1$-$C_6$-alkyl, $C_3$-$C_6$-cycloalkyl and $C_1$-$C_2$-fluoroalkyl.

9. The compound of the formula I of claim 1 of the formula Ia,

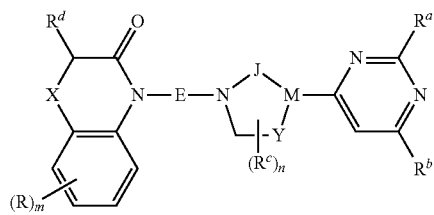

(Ia)

in which n, X, E, J, M, R, $R^a$, $R^b$, $R^c$ and $R^d$ have the aforementioned meanings, and m is 0, 1, 2 or 3.

10. The compound of claim 1 of the formula Ib,

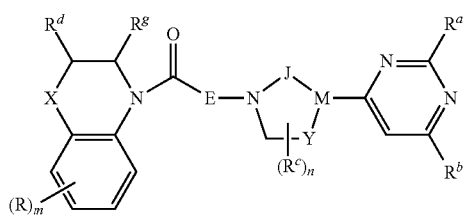

(Ib)

in which n, X, E, J, M, R, $R^a$, $R^b$, $R^c$ and $R^d$ and $R^g$ have the aforementioned meanings, and m is 0, 1, 2 or 3.

11. The compound of claim 1 of the formula Ic,

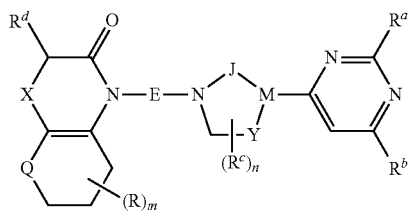

(Ic)

in which n, X, E, J, M, R, $R^a$, $R^b$, $R^c$ and $R^d$ have the aforementioned meanings, Q is $CH_2$ or C=O, and m is 0, 1, 2 or 3.

12. The compound of claim 1 of the formula Id,

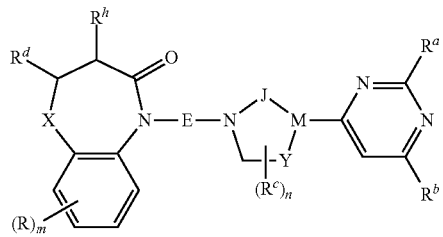

(Id)

in which n, X, E, J, M, R, $R^a$, $R^b$, $R^c$, $R^d$ and $R^h$ have the aforementioned meanings, and m is 0, 1, 2 or 3.

13. The compound of claim 1 of the formula Ie,

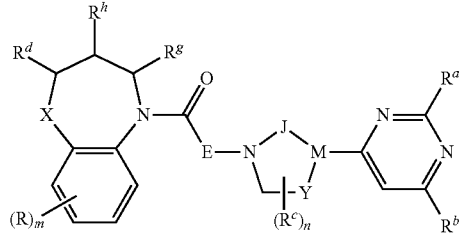

(Ie)

in which n, X, E, J, M, R, $R^a$, $R^b$, $R^c$, $R^d$, $R^g$ and $R^h$ have the aforementioned meanings, and m is 0, 1, 2 or 3.

14. A pharmaceutical composition comprising a compound of the formula I according to claim 1 or a physiologically tolerated acid addition salt thereof, together with a physiologically acceptable carrier and/or excipient.

15. A method for the treatment of schizophrenia and/or depression, the method comprising administering to a subject in need thereof a therapeutically effective amount of a compound of formula (I) according to claim 1, or a physiologically acceptable acid addition salt thereof.

* * * * *